United States Patent [19]

Selby

[11] Patent Number: 4,740,229

[45] Date of Patent: Apr. 26, 1988

[54] CYANOHETEROCYCLIC SULFONYLUREAS

[75] Inventor: Thomas P. Selby, Hockessin, Del.

[73] Assignee: E. I. Du Pont de Nemours and Company, Wilmington, Del.

[21] Appl. No.: 856,301

[22] Filed: May 1, 1986

Related U.S. Application Data

[63] Continuation-in-part of Ser. No. 742,423, Jun. 7, 1985, abandoned.

[51] Int. Cl.$^4$ .................... A01N 43/02; C07D 401/00
[52] U.S. Cl. ............................................ 71/90; 71/91; 71/92; 71/93; 544/208; 544/209; 544/211; 544/212; 544/253; 544/278; 544/296; 544/320; 544/321; 544/323; 544/224; 544/331; 544/332; 546/276; 548/267; 548/268

[58] Field of Search ............... 544/320, 321, 324, 323, 544/331-332; 71/92, 90, 91

[56] References Cited

U.S. PATENT DOCUMENTS 4,342,587  8/1982  Levitt ................................. 544/331
4,604,130  8/1986  Shapiro ............................... 544/320

Primary Examiner—Glennon M. Hollrah
Assistant Examiner—James H. Turnipseed

[57] ABSTRACT

Cyanoheterocyclic sulfonylureas and agricultural compositions containing them are useful as general preemergence or postemergence herbicides or plant growth regulants.

28 Claims, No Drawings

CYANOHETEROCYCLIC SULFONYLUREAS

RELATED APPLICATION

This application is a continuation-in-part of copending application U.S. Ser. No. 742,423, filed June 7, 1985, now abandoned.

BACKGROUND OF THE INVENTION

South African Patent Application No. 83/4956 (German Priority 7/8/82) discloses, in part, herbicidal sulfonylureas of the formula

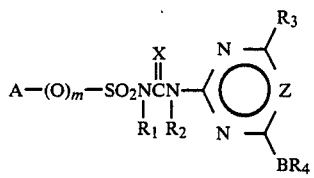

wherein
A is, interalia, a radical of the formula $(R_6)_p$

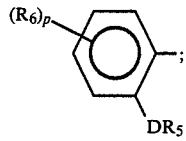

m is 0 or 1;
X is O or S;
$R_1$ is H or $C_1-C_4$ alkyl;
$R_2$ is H, $C_1-C_4$ alkyl or phenyl;
$R_3$ is, inter alia, H, halogen, $NO_2$, CN, $C_1-C_4$ alkylamino, etc.;
B and D are independently a single bond or a methylene or ethylene group;
$R_4$ is a radical of the formula $C(O)R_7$ and "functional derivatives" derived from said carbonyl group such as acetals, ketals, etc.;
$R_5$ is, inter alia, halogen, $NO_2$, $C_1-C_4$ alkyl, etc.; and
$R_6$ is, inter alia, halogen, $CF_3$, $NO_2$, etc.

U.S. Pat. No. 4,342,587 (issued 8/3/82) teaches herbicidal sulfonylureas of the formula

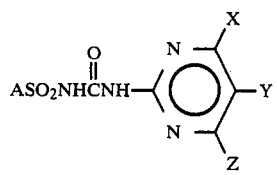

wherein
A is

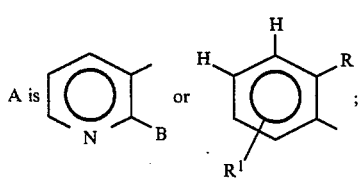

X and Z are independently H, $CH_3$, Br, Cl, $OCH_3$, $C_2H_5$, $CH_2OCH_3$ or $OC_2H_5$;
Y is, inter alia, F, Cl, Br, I, $CH_3$, $C_2H_5$, $C_3H_7$, $C_4H_9$, $CH_2CH=CH_2$, CN, $OCH_3$, $OC_2H_5$, etc.;
B is Cl or Br; and
R is, inter alia, $CO_2R^2$, $C(O)NR_a^2R_b^2$, Cl, $CF_3$, $NO_2$, etc.

European Patent Application EP-A-No. 107,979 (published 5/9/84) discloses, in part, herbicidal sulfonylureas of the formula

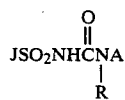

wherein
J is, inter alia,

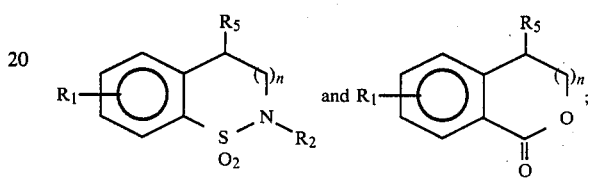

A is, inter alia,

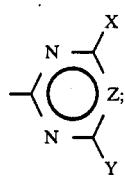

$R_1$ is H, F, Cl, Br, $CH_3$, $OCH_3$, $CF_3$, $SCH_3$ or $OCF_2H$;
Z is CH, N, $CCH_3$, $CC_2H_5$, CCl or CBr;
X is $CH_3$, $OCH_3$, $OC_2H_5$, Cl, F, Br, $OCF_2H$, $CH_2F$ or $CR_3$;
Y is, inter alia, H, $CH_3$, $OCH_3$, $OC_2H_5$, $C_2H_5$, $CH_2OCH_3$, CN, $CH_2SCH_3$, $CF_3$, $SCH_3$, etc.;
$R_2$ is H or $C_1-C_4$ alkyl;
$R_5$ is H or $CH_3$; and
n is 0, 1 or 2.

European Patent Application No. EP-A-No. 125,864 (published 11/21/84) covers herbicidal sulfonylureas of the formula

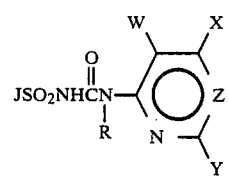

wherein
J is, inter alia,

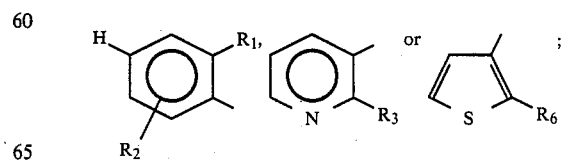

$R_1$ is $NO_2$, F, Cl, Br, $CF_3$, $C_1-C_3$ alkyl, etc.;
$R_2$ is H, Cl, F, Br, $CH_3$, $OCH_3$ or $CF_3$;

Z is CH or N;
X is CH₃, OCH₃, OC₂H₅, CH₂OCH₃ or Cl;
Y is CH₃, OCH₃, OC₂H₅ or Cl; and
W is CN, CO₂CH₃, CO₂C₂H₅, NO₂, S(O)R₁₁, SO₂R₁₁ or C(O)NR₁₄R₁₅.

SUMMARY OF THE INVENTION

This invention relates to novel compounds of Formula I, suitable agricultural compositions containing them, and their method-of-use as general preemergence and/or postemergence herbicides or plant growth regulants.

$$JSO_2NHCNA \overset{W}{\underset{R}{\|}} \quad I$$

wherein
W is O or S;
R is H or CH₃;
A is

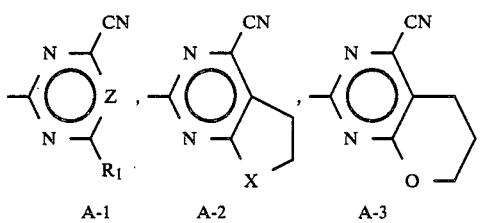

A-1    A-2    A-3

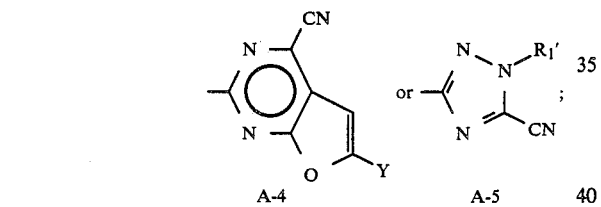

A-4    A-5

R₁ is H, C₁–C₃ alkyl, C₁–C₃ alkoxy, C₁–C₃ haloalkoxy, C₁–C₃ haloalkyl, C₁–C₃ haloalkylthio, C₁–C₃ alkylthio, halogen, C₂–C₅ alkoxyalkyl, C₂–C₅ alkoxyalkoxy, amino, C₁–C₂ alkylamino, N(CH₃)₂, C₃ alkenyloxy, C₃ alkynyloxy, C₂–C₃ alkylthioalkyl, C₂–C₃ alkylsulfinylalkyl, C₂–C₃ alkylsulfonylalkyl, cyclopropyl, C₂–C₃ alkynyl,

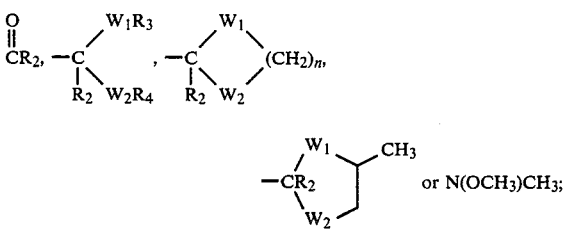

or N(OCH₃)CH₃;

R'₁ is H, C₁–C₆ alkyl or CH₂CF₃;
X is O or CH₂;
Y is H or CH₃;
W₁ and W₂ are independently O or S;
Z is CH or N;
R₂ is H or CH₃;
R₃ is C₁–C₂ alkyl;
R₄ is C₁–C₂ alkyl;
n is 2 or 3;

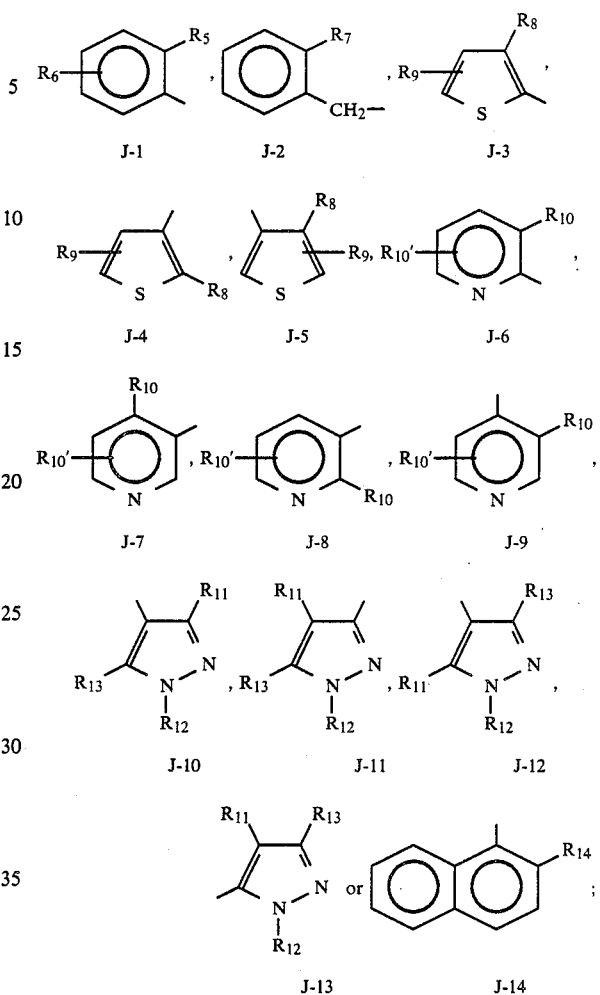

J-1    J-2    J-3
J-4    J-5    J-6
J-7    J-8    J-9
J-10   J-11   J-12
J-13   J-14

R₅ is F, Cl, Br, NO₂, C₁–C₄ alkyl, C₂–C₄ alkenyl, C₂–C₄ haloalkenyl, C₂–C₄ alkynyl, C₁–C₄ haloalkyl, C₁–C₄ alkoxy, OCH₂CH₂OCH₃, C₁–C₄ haloalkoxy, C₃–C₄ alkenyloxy, C₂–C₄ haloalkenyloxy, C₃–C₄ alkynyloxy, CO₂R₁₅, CONR₁₆R₁₇, SO₂N(OCH₃)CH₃, SO₂NR₁₆R₁₇, S(O)ₘR₁₈, OSO₂R₁₉, C₁–C₂ alkyl substituted with C₁–C₂ alkoxy or C₁–C₂ alkylthio, CH₂CN, phenyl, C(O)R₂₀, CR₂₀(OR₂₁)₂,

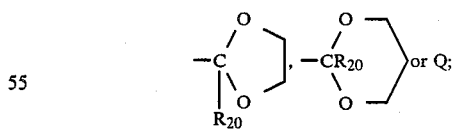

or Q;

m is 0, 1 or 2;
Q is

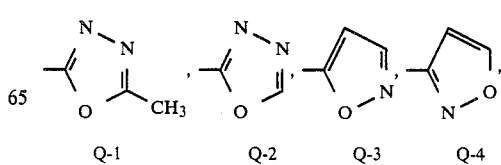

Q-1    Q-2    Q-3    Q-4

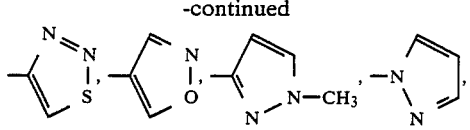

Q-5    Q-6    Q-7    Q-8

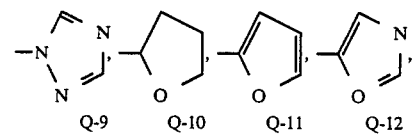

Q-9    Q-10    Q-11    Q-12

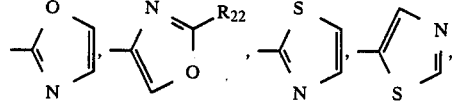

Q-13    Q-14    Q-15    Q-16

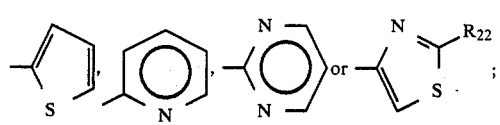

Q-17    Q-18    Q-19    Q-20

$R_6$ is H, Cl, Br, F, CN, $C_1$–$C_3$ alkyl, $C_1$–$C_3$ alkoxy, $C_1$–$C_3$ alkylthio, $C_1$–$C_3$ haloalkyl, nitro, $C_1$–$C_3$ haloalkylthio, $C_1$–$C_3$ haloalkoxy, $C_1$–$C_3$ alkylsulfinyl, $C_1$–$C_3$ alkylsulfonyl, amino, $C_1$–$C_3$ alkylamino, di($C_1$–$C_2$)alkylamino, $CH_2OCH_3$ or $CH_2SCH_3$;

$R_7$ is Cl, $NO_2$, $CO_2CH_3$, $CO_2C_2H_5$, $SO_2N(CH_3)_2$, $OSO_2CH_3$, $SO_2CH_3$, $SO_2C_2H_5$, $OCH_3$ or $OC_2H_5$;

$R_8$ is $C_1$–$C_3$ alkyl, $C_1$–$C_2$ alkoxy, R, Cl, Br, $NO_2$, $CO_2R_{15}$, $SO_2NR_{16}R_{17}$, $SO_2N(OCH_3)CH_3$, $C(O)NR_{16}R_{17}$, $S(O)_mR_{18}$ or $C_2$–$C_4$ haloalkenyl;

$R_9$ is H, F, Cl or $CH_3$;

$R_{10}$ is $C_1$–$C_2$ alkyl, $C_1$–$C_2$ alkoxy, F, Cl, Br, $SO_2NR_{16}R_{17}$, $SO_2N(OCH_3)CH_3$, $S(O)_mR_{18}$, $C(O)NR_{16}R_{17}$, $C_3$–$C_4$ alkenyloxy, $CH_2OCH_3$, $CH_2OC_2H_5$, $C_1$–$C_2$ alkylamino, di($C_1$–$C_2$)alkylamino or $COOR_{23}$;

$R'_{10}$ is H, F, Cl or $CH_3$;

$R_{11}$ is $C_1$–$C_3$ alkyl, F, Cl, Br, $NO_2$, $CO_2R_{15}$, $SO_2NR_{16}R_{17}$, $SO_2R_{18}$, $OCF_2H$ or phenyl;

$R_{12}$ is H, $C_1$–$C_3$ alkyl, $CH_2CH=CH_2$ or phenyl;

$R_{13}$ is H, Cl, F, Br or $C_1$–$C_3$ alkyl;

$R_{14}$ is H, $CH_3$, $OCH_3$, F, Cl, Br, $SO_2N(CH_3)_2$, $OSO_2CH_3$ or $S(O)_mCH_3$;

$R_{15}$ is $C_1$–$C_4$ alkyl, $C_3$–$C_4$ alkenyl, $C_3$–$C_4$ alkynyl, $CH_2CH_2Cl$, $CH_2CH_2F$, $CH_2CF_3$, or $C_1$–$C_2$ alkyl substituted with $OCH_3$ or $SCH_3$;

$R_{16}$ is H or $C_1$–$C_3$ alkyl;

$R_{17}$ is H or $C_1$–$C_3$ alkyl;

$R_{18}$ is $C_1$–$C_3$ alkyl, $CH_2CH=CH_2$, $CH_2C\equiv CH$ or $C_1$–$C_3$ haloalkyl;

$R_{19}$ is $C_1$–$C_3$ alkyl or $N(CH_3)_2$;

$R_{20}$ is H, $C_1$–$C_4$ alkyl, $C_3$–$C_4$ alkenyl, $C_3$–$C_4$ alkynyl, $C_3$–$C_6$ cycloalkyl, $CH_2CH_2Cl$, $CH_2CH_2F$, $CH_2CF_3$ or $C_1$–$C_2$ alkyl substituted with $OCH_3$ or $SCH_3$;

$R_{21}$ is $C_1$–$C_2$ alkyl;

$R_{22}$ is H or $CH_3$; and $R_{23}$ is $C_1$–$C_3$ alkyl or allyl; and their agriculturally suitable salts;

provided that (1) when W is S, then A is A-1, R is H, and $R_1$ is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$, $CH(OCH_3)_2$

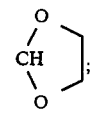

(2) when J is J-1 and A is A-1, then $R_1$ is other than

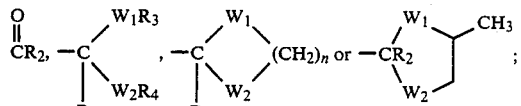

(3) when $R_1$ is $C_1$ haloalkoxy, then Z is CH;
(4) when J is J-10, then $R_{11}$ and $R_{12}$ are not both phenyl; and
(5) when $R_1$ is halogen, Z is CH.

In the above definitions, the term "alkyl" used either alone or in compound words such as "alkylthio" or "haloalkyl", denotes straight chain or branched alkyl, e.g., methyl, ethyl, n-propyl, isopropyl or the different butyl isomers.

Alkoxy denotes methoxy, ethoxy, n-propoxy, isopropoxy and the different butoxy isomers.

Alkenyl denotes straight chain or branched alkenes, e.g., vinyl, 1-propenyl, 2-propenyl, 3-propenyl and the different butenyl isomers.

Alkynyl denotes straight chain or branched alkynes, e.g., ethynyl, 1-propynyl, 2-propynyl and the different butynyl isomers.

Cycloalkyl denotes cyclopropyl, cyclobutyl, cyclopentyl and cyclohexyl.

The term "halogen", either alone or in compound words such as "haloalkyl", denotes fluorine, chlorine, bromine or iodine.

In terms such as $C_2$–$C_3$ alkylthioalkyl, the specified number of carbon atoms is meant to define the total number of carbon atoms in that substituent group. For example, $C_2$–$C_3$ alkylthioalkyl would designate $CH_2SCH_3$, $CH_2SC_2H_5$, $CH_2CH_2SCH_3$ or $CH(CH_3)SCH_3$, and $C_2$–$C_5$ alkoxyalkoxy would represent $OCH_2OCH_3$ through $O(CH_2)_4OCH_3$ or $OCH_2O(CH_2)_3$ and the various structural isomers embraced therein.

Preferred for reasons of greater ease of synthesis and/or greater herbicidal efficacy are:

(1) Compounds of Formula I where W is O and R is H.
(2) Compounds of Preferred 1 where $R_5$ is Cl, Br, $NO_2$, $C_1$–$C_3$ alkyl, $C_2$–$C_3$ alkenyl, $C_2$–$C_3$ haloalkenyl, $C_2$–$C_3$ alkynyl, $C_1$–$C_3$ haloalkyl, $C_1$–$C_3$ alkoxy, $OCH_2CH_2OCH_3$, $C_1$–$C_3$ haloalkoxy, $C_3$ alkenyloxy, $C_2$–$C_3$ haloalkenyloxy, $C_3$ alkynyloxy, $CO_2R_{15}$, $CONR_{16}R_{17}$, $SO_2N(OCH_3)CH_3$, $SO_2NR_{16}R_{17}$, $S(O)_mR_{18}$, $OSO_2R_{19}$, $C_1$–$C_2$ alkyl substituted with $C_1$–$C_2$ alkoxy or $C_1$–$C_2$ alkylthio, $CH_2CN$, phenyl, $C(O)R_{20}$, $CR_{20}(OR_{21})_2$,

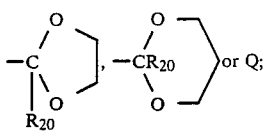

$R_6$ is H, Cl, Br, F, $CH_3$, $C_2H_5$, $OCH_3$, $OC_2H_5$, $SCH_3$, $SC_2H_5$, $C_1$-$C_2$ haloalkyl, CN, $CH_2OCH_3$ or $CH_2SCH_3$; and $R_6$ must be H when para to the sulfonylurea bridge, $SO_2NHC(W)NRA$;

Q is Q-1, Q-2, Q-5, Q-12, Q-13, Q-14, Q-15, Q-16 or Q-20;

$R_7$ is $CO_2CH_3$, $CO_2C_2H_5$, $SO_2N(CH_3)_2$, $SO_2CH_3$, $SO_2C_2H_5$;

$R_8$ is $C_1$-$C_2$ alkyl, Cl, Br, $NO_2$, $CO_2R_{15}$, $SO_2NR_{16}R_{17}$, $S(O)_mR_{18}$ or $C_2$-$C_4$ haloalkenyl;

$R_{10}$ is $C_1$-$C_2$ alkyl, $C_1$-$C_2$ alkoxy, Cl, Br, $SO_2NR_{16}R_{17}$, $S(O)_mR_{18}$, $OCH_2CH=CH_2$, $(CH_3)_2N$, $CH_3NH$ or $COOR_{23}$;

$R_{11}$ is $C_1$-$C_2$ alkyl, Cl, Br, $NO_2$, $CO_2R_{15}$, $SO_2NR_{16}R_{17}$ or $SO_2R_{18}$;

$R_{12}$ is H or $C_1$-$C_2$ alkyl;

$R_{13}$ is H, Cl, F or $CH_3$;

$R_{15}$ is $C_1$-$C_3$ alkyl, $CH_2CH=CH_2$ or $CH_2C≡CH$;

$R_{16}$ and $R_{17}$ are independently H, $CH_3$ or $C_2H_5$;

$R_{18}$ is $C_1$-$C_3$ alkyl or $C_1$-$C_3$ haloalkyl; and $R_{20}$ is H, $C_1$-$C_3$ alkyl, $C_3$-$C_4$ cycloalkyl, $CH_2CH=CH_2$ or $CH_2C≡CH$.

(3) Compounds of Preferred 2 where $R_1$ is $C_1$-$C_2$ alkyl, $C_1$-$C_2$ alkoxy, $C_1$-$C_2$ haloalkoxy, $C_1$-$C_2$ haloalkyl, $C_1$-$C_2$ haloalkylthio, $C_1$-$C_2$ alkylthio, $C_2$-$C_3$ alkoxyalkyl, $C_2$-$C_4$ alkoxyalkoxy, $C_2$-$C_3$ alkylthioalkyl, $C_2$-$C_3$ alkylsulfinylalkyl, $C_2$-$C_3$ alkylsulfonylalkyl, cyclopropyl or C≡CH.

(4) Compounds of Preferred 3 where A is A-1.
(5) Compounds of Preferred 3 where A is A-2.
(6) Compounds of Preferred 3 where A is A-3.
(7) Compounds of Preferred 3 where A is A-4.
(8) Compounds of Preferred 3 where A is A-5.
(9) Compounds of Preferred 4 where J is J-1 and $R_6$ is in the 5-position.
(10) Compounds of Preferred 4 where J is J-2.
(11) Compounds of Preferred 4 where J is J-3 and $R_9$ is H.
(12) Compounds of Preferred 4 where J is J-4 and $R_9$ is H.
(13) Compounds of Preferred 4 where J is J-5 and $R_9$ is H.
(14) Compounds of Preferred 4 where J is J-6.
(15) Compounds of Preferred 4 where J is J-7.
(16) Compounds of Preferred 4 where J is J-8.
(17) Compounds of Preferred 4 where J is J-9.
(18) Compounds of Preferred 4 where J is J-10.
(19) Compounds of Preferred 4 where J is J-11.
(20) Compounds of Preferred 4 where J is J-12.
(21) Compounds of Preferred 4 where J is J-13.
(22) Compounds of Preferred 4 where J is J-14.

Specifically preferred for reasons of their highest herbicidal activity, greatest plant growth regulant activity and/or most favorable ease of synthesis is 2-[[(4-cyano-6-methylpyrimidin-2-yl)aminocarbonyl-]aminosulfonyl]benzoic acid, methyl ester, m.p. 208°–213° C., d; and 3-[[(4-cyano-6-methoxypyrimidin-2-yl)aminocarbonyl-]aminosulfonyl]2-thiophene carboxylic acid, methyl ester, m.p. 89°–92° C.

DETAILED DESCRIPTION OF THE INVENTION

Synthesis

The compounds of Formula I may be prepared by one or more of the methods described below. Specifically, the compounds of Formula I may be prepared by the reaction of an appropriately substituted sulfonyl isocyanate (W=O) or a sulfonylisothiocyanate (W=S) with an appropriate heterocyclic amine as taught in U.S. Pat. Nos. 4,398,939 and 4,394,506. Compounds of Formula I, where $R_5$, $R_7$ and $R_8$ are other than $CO_2R_{15}$, can also be prepared by reacting sulfonamides with an appropriate methyl carbamate in the presence of an equimolar amount of trimethylaluminum as taught in U.S. Pat. Nos. 4,398,939 and 4,394,506. The required carbamates are prepared by reacting the corresponding amines with dimethyl carbonate or methyl chloroformate in the presence of a strong base.

Alternatively, compounds of Formula I can be prepared by reacting a sulfonylphenyl carbamate with an appropriate amine as taught in U.S. Pat. No. 4,443,245. The requisite sulfonylcarbamates are prepared by reacting the corresponding sulfonamides with diphenylcarbonate in the presence of a strong base. Compounds of Formula I can also be prepared by reacting a sulfonamide with an appropriate heterocyclic phenylcarbamate in the presence of a nonnucleophilic base by methods taught in EPO Publication No. 44807. The required carbamates are prepared by reacting the corresponding heterocyclic amines with phenylcarbonate in the presence of a base.

Intermediate sulfonyl isocyanates can be prepared by methods taught in U.S. Pat. No. 4,238,621, by a procedure taught by Ulrich and Sayigh, *Newer Methods of Preparative Organic Chemistry*, Vol. VI, pp. 223–241, Academic Press, New York and London, W. Foerst, Ed., or according to the teachings of Japanese Pat. No. 76,126,816 (Chem. Abst. 85: 77892e [1976]). Intermediate sulfonyl isothiocyanates can be prepared as taught in U.S. Pat. No. 4,394,506 and according to the teachings of K. Kartke, Arch. Pharm., 299, 174 (1966).

Intermediate sulfonamides can be prepared from the corresponding sulfonyl chlorides by contacting with anhydrous or aqueous ammonia.

The preparation of sulfonamides from sulfonyl chlorides is widely reported in the literature. For reviews, see F. Hawking and J. S. Lawrence, "The Sulfonamides." H. K. Lewis and Co., London, 1950 and E. H. Northey, "The Sulfonamides and Allied Compounds," Reinbold Publishing Corp., New York, 1948.

The required sulfonyl chlorides may be synthesized by known methods or with slight modifications thereof, by one skilled in the art. Several representative teachings are listed below. Sulfonyl chlorides, where J is J-1, are generally described in U.S. Pat. No. 4,127,405 and more specifically for o-esters in U.S. Pat. No. 4,394,506; o-sulfonamides in U.S. Pat. No. 4,310,346; o-heterocycles in EPO Publication No. 83,975 and EPO Publication No. 23,422; o-sulfonates in U.S. Pat. No. 4,435,205. Additionally, sulfonyl chlorides where J is J-2, J-3 to J-5, J-6 to J-7, J-8 to J-11 and J-12 can be made according to the teachings in U.S. Pat. Nos. 4,420,325, 4,441,910, 4,398,939, 4,481,029, EPO Publication No. 13,480, U.S. Pat. No. 4,456,469, EPO Publication No. 95,925 and U.S. Pat. No. 4,370,479.

Heterocycles of Formula II may be synthesized as shown in Equation 1 by the addition of cyanide to the compounds of Formula III.

Equation 1

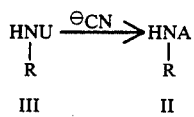

wherein
R and A are as previously defined;
U is

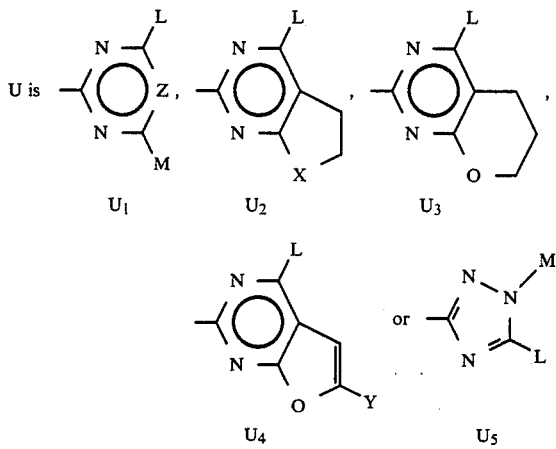

L is Cl, Br or I;
M is $C_1$–$C_3$ alkyl, $C_2$–$C_5$ alkoxyalkyl, $C_2$–$C_3$ alkylthioalkyl, $C_2$–$C_3$ alkylsulfinylalkyl, $C_2$–$C_3$ alkylsulfonylalkyl, cyclopropyl,

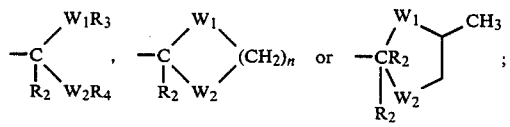

M' is $C_1$–$C_6$ alkyl or $CH_2CF_3$.

The reaction of Equation 1 is carried out at 20° to 160° C. for 0.5 to 48 hours by mixing the haloheterocycle of Formula III with cuprous or potassium cyanide (one or more equivalents) in a solvent such as dimethylformamide, dimethylsulfoxide or acetonitrile.

The requisite haloheterocycles of Formula III where U is $U_1$ and M is cyclopropyl can be prepared as taught in South African Patent Application 83/7434. The haloheterocycle of Formula $U_1$, where M is acetal, thioacetal, ketal or thioketal, can be prepared as taught in EPO Publication No. 84,224. The synthesis of the bicyclicamines, where U is $U_2$ or $U_3$, is taught in U.S. Pat. No. 4,339,267. The synthesis of bicyclicamines, where U is $U_4$, is taught in U.S. Pat. No. 4,487,626.

The halotriazoles of Formula $U_5$ can be prepared as described in "The Chemistry of Heterocyclic Compounds," Vol. 37, John Wiley and Sons, New York (1981).

Other required haloheterocycles of Formula III where U is $U_1$, are either known or can be prepared by methods known to one skilled in the art.

For a review of the synthesis and reactions of 2-aminopyrimidines (III, U is $U_1$ and Z=CH), see "The Chemistry of Heterocyclic Compounds", Vol. 16, John Wiley and Sons, New York (1962). For a review of the synthesis and reactions of 2-amino-s-triazines (III, U is $U_1$ and Z=N), see "The Chemistry of Heterocyclic Compounds", Vol. 13, John Wiley, New York (1959), F. C. Schaefer, U.S. Pat. No. 3,154,547 and F. C. Schaefer and K. R. Huffman, *J. Org. Chem.*, 28, 1812 (1963).

Heterocycles of Formula IV can be synthesized by the route shown in Equation 2 where an appropriate nucleophile T is added to the compounds of Formula V.

Equation 2

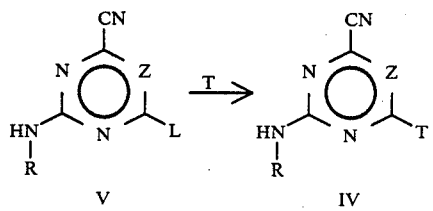

wherein
R, L and Z are as previously defined; and
T is $C_1$–$C_3$ alkoxy, $C_1$–$C_3$ alkylthio, $C_2$–$C_5$ alkoxyalkoxy, amino, $C_1$–$C_2$ alkylamino, dimethylamino, $C_3$ alkenyloxy, $C_3$ alkynyloxy, $C_2$–$C_3$ alkynyl and methoxymethylamino.

The reaction is carried out at 0° to 100° C. for 1 to 48 hours by mixing the haloheterocycle of Formula V with the appropriate nucleophile and base, or the potassium or sodium salt of the appropriate nucleophile (one or more equivalents) in a solvent such as an alcohol, acetone, dioxane or tetrahydrofuran.

Heterocycles of Formula V may be prepared by the reaction of phosphorus oxychloride with the compounds of Formula VI as shown in Equation 3.

Equation 3

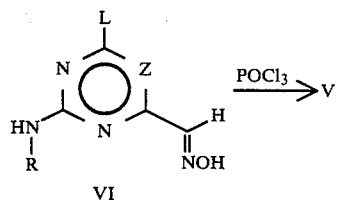

wherein
R, L and Z are as previously defined.

The reaction of Equation 3 is carried out at reflux for 3 to 24 hours by mixing the oximeheterocycle of Formula VI with phosphorus oxychloride.

The required haloheterocycles of Formula VI are either known or can be prepared by methods known to one skilled in the art.

Heterocycles of Formula VII may be prepared by the synthetic route shown in Equation 4.

Equation 4

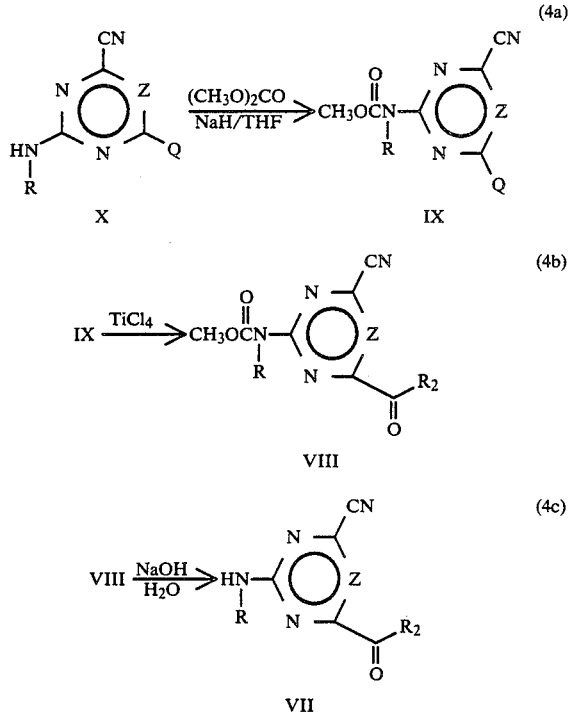

wherein
Q is

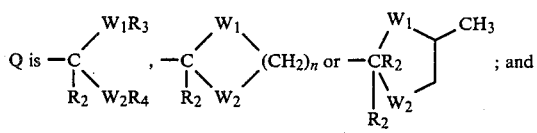

and
R, $R_2$, $R_3$, $R_4$, $W_1$, $W_2$, n and Z are as previously defined.

The reaction of Equation 4a can be carried out by mixing compounds of Formula X with one equivalent each of sodium hydride and dimethylcarbonate for 1–3 days in a solvent such as tetrahydrofuran or dimethylformamide. The reaction of Equation 4b is performed by adding a Lewis acid such as titanium tetrachloride to compounds of Formula IX in a solvent such as methylene chloride and stirring at room temperature for 0.5 hours to 3 days. The reaction of Equation 4c is carried out by contacting compounds of Formula VIII with aqueous alkali for 10–100 minutes at 20°–80° C. and extracting the product into an organic solvent.

Heterocyclic amines of Formula II where A is A-1, $R_1$ is H and Z is CH or N may be synthesized by a method similar to that taught by D. J. Brown, W. B. Cowden and L. Strekowski, *Aust. J. Chem.*, 34, 1353 (1981).

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide or carbonate). Quaternary amine salts can be made by similar techniques.

Salts of compounds of Formula I can also be prepared by exchange of one cation for another. Cationic exchange can be effected by direct contact of an aqueous solution of a salt of a compound of Formula I (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble, e.g., a potassium sodium or calcium salt.

Acid addition salts, useful in this invention, can be obtained by reacting a compound of Formula I with a suitable acid, e.g., p-toluenesulfonic acid, trichloroacetic acid or the like.

The preparation of the compounds of this invention is further illustrated by the following example.

EXAMPLE 1

2[[(4-Cyano-6-methylpyrimidin-2-yl)aminocarbonyl-]aminosulfonyl]benzoic acid, methyl ester 2-Amino-4-cyano-6-methylpyrimidine, 0.2 g, was mixed with 2-carbomethoxybenzenesulfonyl isocyanate, 0.7 g, in 8 ml of dry methylene chloride. After five minutes a thick precipitate formed and the reaction mixture was stirred at room temperature overnight. The reaction mixture was filtered and the filtrate stripped to give 0.3 g of the title compound as a solid, m.p. 208°–213° C. (dec). NMR ($CF_3CO_2D$): δ2.95 (s, 3H), 4.05 (s, 3H), 7.85 (s, 1H), 7.88–8.15 (m), 8.25–8.65 (m).

EXAMPLE 2

3-[[(4-Cyano-6-methoxypyrimidin-2-yl)aminocarbonyl-]aminosulfonyl]-2-thiophenecarboxylic acid, methyl ester 2-Amino-4-cyano-6-methoxypyrimidine, 0.1 g, was mixed with 2-carbomethoxythiophene-3-sulfonyl isocyanate, 0.165 g, in 10 ml of methylene chloride. The reaction mixture was stirred at room temperature overnight. The reaction mixture was stripped to yield 0.19 g of the title compound as a solid, m.p. 89°–92° C. (dec). NMR ($CDCl_3$): δ6.89 (s, 3H), 4.20 (s, 3H), 6.83 (s, 1H), 7.59 (d, 1H), 7.80 (d, 1H).

Using the methods taught in Equations 1–4 and Examples 1 and 2, one skilled in the art can prepare the following compounds of Tables I–XI.

Key of General Structures

The following structures are designated as shown in Tables I–XI.

| General Structure I | 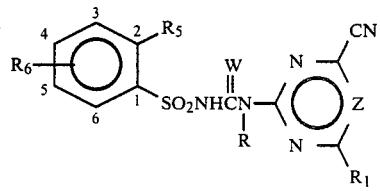 |
|---|---|

| | |
|---|---|
| General Structure II | 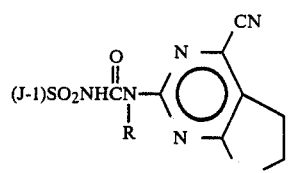 |
| General Structure III | 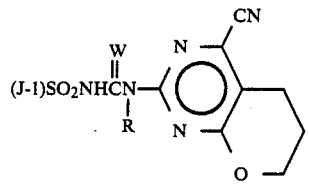 |
| General Structure IV | 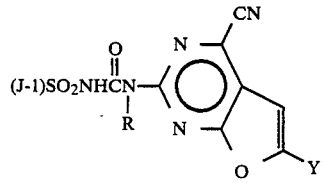 |
| General Structure V | 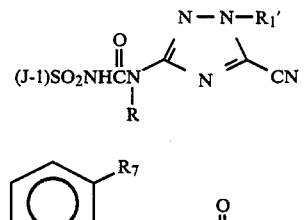 |
| General Structure VI | 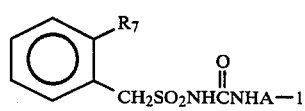 |
| General Structure VII | 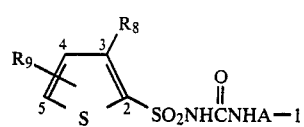 |
| General Structure VIII | 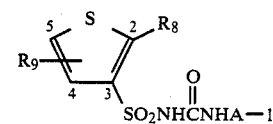 |
| General Structure IX | 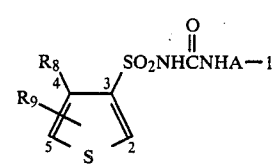 |
| General Structure X |  |
| General Structure XI | 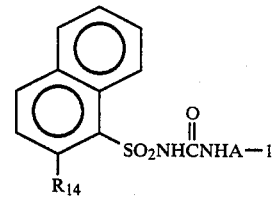 |

TABLE I

| | | General Formula I | | | | |
|---|---|---|---|---|---|---|
| $R_5$ | $R_6$ | W | R | $R_1$ | Z | m.p. (°C.) |
| $CO_2CH_3$ | H | O | H | $CH_3$ | CH | 203–213(d) |
| $CO_2CH_3$ | H | O | H | $CH_3$ | N | |
| $CO_2CH_3$ | H | S | H | $CH_3$ | CH | |
| $CO_2CH_3$ | H | S | H | $CH_3$ | N | |
| $CO_2CH_3$ | H | O | $CH_3$ | $CH_3$ | CH | |
| $CO_2CH_3$ | H | O | $CH_3$ | $CH_3$ | N | |
| $CO_2CH_3$ | 5-Cl | O | H | $CH_3$ | CH | |
| $CO_2CH_3$ | 5-Cl | O | H | $CH_3$ | N | |
| $CO_2CH_3$ | 5-Br | O | H | $CH_3$ | CH | |
| $CO_2CH_3$ | 5-Br | O | H | $CH_3$ | N | |
| $CO_2CH_3$ | 5-$OCH_3$ | O | H | $CH_3$ | CH | |
| $CO_2CH_3$ | 5-$OCH_3$ | O | H | $CH_3$ | N | |
| $CO_2CH_3$ | 5-$OC_2H_5$ | O | H | $CH_3$ | CH | |
| $CO_2CH_3$ | 5-$OC_2H_5$ | O | H | $CH_3$ | N | |
| $CO_2CH_3$ | 5-$SCH_3$ | O | H | $CH_3$ | CH | |
| $CO_2CH_3$ | 5-$SCH_3$ | O | H | $CH_3$ | N | |
| $CO_2CH_3$ | 5-$CH_3$ | O | H | $CH_3$ | CH | |
| $CO_2CH_3$ | 5-$CH_3$ | O | H | $CH_3$ | N | |
| $CO_2CH_3$ | 5-CN | O | H | $CH_3$ | CH | |
| $CO_2CH_3$ | 5-CN | O | H | $CH_3$ | N | |
| $CO_2CH_3$ | 5-$CH_2OCH_3$ | O | H | $CH_3$ | CH | |
| $CO_2CH_3$ | 5-$CH_2OCH_3$ | O | H | $CH_3$ | N | |
| $CO_2CH_3$ | 5-$OCF_2H$ | O | H | $CH_3$ | CH | |
| $CO_2CH_3$ | 5-$OCF_2H$ | O | H | $CH_3$ | N | |
| $CO_2C_2H_5$ | 5-Cl | O | H | $CH_3$ | CH | |
| $CO_2C_2H_5$ | 5-Cl | O | H | $CH_3$ | N | |
| $CO_2C_2H_5$ | 5-Br | O | H | $CH_3$ | CH | |
| $CO_2C_2H_5$ | 5-Br | O | H | $CH_3$ | N | |
| $CO_2C_2H_5$ | 5-$OCH_3$ | O | H | $CH_3$ | CH | |
| $CO_2C_2H_5$ | 5-$OCH_3$ | O | H | $CH_3$ | N | |
| $CO_2C_2H_5$ | H | O | H | $CH_3$ | CH | |
| $CO_2C_2H_5$ | H | O | H | $CH_3$ | N | |
| $CO_2C_2H_5$ | 5-$OC_2H_5$ | O | H | $CH_3$ | CH | |
| $CO_2C_2H_5$ | 5-$OC_2H_5$ | O | H | $CH_3$ | N | |
| $CO_2C_2H_5$ | 5-$SCH_3$ | O | H | $CH_3$ | CH | |

TABLE I-continued

General Formula I

| R₅ | R₆ | W | R | R₁ | Z | m.p. (°C.) |
|---|---|---|---|---|---|---|
| CO₂C₂H₅ | 5-SCH₃ | O | H | CH₃ | N | |
| CO₂C₂H₅ | 5-CH₃ | O | H | CH₃ | CH | |
| CO₂C₂H₅ | 5-CH₃ | O | H | CH₃ | N | |
| CO₂C₂H₅ | 5-CN | O | H | CH₃ | CH | |
| CO₂C₂H₅ | 5-CN | O | H | CH₃ | N | |
| CO₂C₂H₅ | 5-OCF₂H | O | H | CH₃ | CH | |
| CO₂C₂H₅ | 5-OCF₂H | O | H | CH₃ | N | |
| CO₂CH₃ | H | O | H | C₂H₅ | CH | |
| CO₂CH₃ | H | O | H | C₂H₅ | N | |
| CO₂CH₃ | 5-Cl | O | H | OCH₃ | CH | |
| CO₂CH₃ | 5-Cl | O | H | OCH₃ | N | |
| CO₂CH₃ | 5-Br | O | H | OCH₃ | CH | |
| CO₂CH₃ | 5-Br | O | H | OCH₃ | N | |
| CO₂CH₃ | 5-OCH₃ | O | H | OCH₃ | CH | |
| CO₂CH₃ | 5-OCH₃ | O | H | OCH₃ | N | |
| CO₂CH₃ | 5-OC₂H₅ | O | H | OCH₃ | CH | |
| CO₂CH₃ | 5-OC₂H₅ | O | H | OCH₃ | N | |
| CO₂CH₃ | 5-SCH₃ | O | H | OCH₃ | CH | |
| CO₂CH₃ | 5-SCH₃ | O | H | OCH₃ | N | |
| CO₂CH₃ | 5-CH₃ | O | H | OCH₃ | CH | |
| CO₂CH₃ | 5-CH₃ | O | H | OCH₃ | N | |
| CO₂CH₃ | 5-CN | O | H | OCH₃ | CH | |
| CO₂CH₃ | 5-CN | O | H | OCH₃ | N | |
| CO₂CH₃ | 5-CH₂OCH₃ | O | H | OCH₃ | CH | |
| CO₂CH₃ | 5-CH₂OCH₃ | O | H | OCH₃ | N | |
| CO₂CH₃ | 5-OCF₂H | O | H | OCH₃ | CH | |
| CO₂CH₃ | 5-OCF₂H | O | H | OCH₃ | N | |
| CO₂CH₃ | H | O | H | OCH₃ | CH | |
| CO₂CH₃ | H | O | H | OCH₃ | N | |
| CO₂CH₃ | H | O | H | OC₂H₅ | CH | |
| CO₂CH₃ | H | O | H | OC₂H₅ | N | |
| CO₂CH₃ | H | O | H | SCH₃ | CH | |
| CO₂CH₃ | H | O | H | SCH₃ | N | |
| CO₂CH₃ | H | O | H | OCH₂CF₃ | CH | |
| CO₂CH₃ | H | O | H | OCH₂CF₃ | N | |
| CO₂CH₃ | H | O | H | CH₂SCH₃ | CH | |
| CO₂CH₃ | H | O | H | CH₂SCH₃ | N | |
| CO₂CH₃ | H | O | H | CH₂SO₂CH₃ | CH | |
| CO₂CH₃ | H | O | H | CH₂SO₂CH₃ | N | |
| CO₂CH₃ | H | O | H | Cl | CH | |
| CO₂CH₃ | H | O | H | Br | CH | |
| CO₂CH₃ | H | O | H | CH₂OCH₃ | CH | |
| CO₂CH₃ | H | O | H | CH₂OCH₃ | N | |
| CO₂CH₃ | H | O | H | OCH₂OCH₃ | CH | |
| CO₂CH₃ | H | O | H | OCH₂OCH₃ | N | |
| CO₂CH₃ | H | O | H | NH₂ | CH | |
| CO₂CH₃ | H | O | H | NH₂ | N | |
| CO₂CH₃ | H | O | H | NHCH₃ | CH | |
| CO₂CH₃ | H | O | H | NHCH₃ | N | |
| CO₂CH₃ | H | O | H | N(CH₃)₂ | CH | |
| CO₂CH₃ | H | O | H | N(CH₃)₂ | N | |
| CO₂CH₃ | H | O | H | N(C₂H₅)₂ | CH | |
| CO₂CH₃ | H | O | H | N(C₂H₅)₂ | N | |
| CO₂CH₃ | H | O | H | OCH₂CH=CH₂ | CH | |
| CO₂CH₃ | H | O | H | OCH₂CH=CH₂ | N | |
| CO₂CH₃ | H | O | H | OCH₂C≡CH | CH | |
| CO₂CH₃ | H | O | H | OCH₂C≡CH | N | |
| CO₂C₃H₇ | H | O | H | CH₃ | CH | |
| CO₂C₃H₇ | H | O | H | CH₃ | N | |
| CO₂CH₂CH=CH₂ | H | O | H | CH₃ | CH | |
| CO₂CH₂CH=CH₂ | H | O | H | CH₃ | N | |
| CO₂CH₃ | H | O | H | cyclopropyl | CH | |
| CO₂CH₃ | H | O | H | cyclopropyl | N | |
| CO₂CH₃ | H | O | H | C≡CH | CH | |
| CO₂CH₃ | H | O | H | C≡CH | N | |
| CO₂CH₃ | H | O | H | C(O)H | CH | |
| CO₂CH₃ | H | O | H | C(O)H | N | |
| CO₂CH₃ | H | O | H | C(O)CH₃ | CH | |
| CO₂CH₃ | H | O | H | C(O)CH₃ | N | |
| CO₂CH₃ | H | O | H | N(OCH₃)CH₃ | CH | |
| CO₂CH₃ | H | O | H | N(OCH₃)CH₃ | N | |
| CO₂CH₃ | H | O | H | HC(OCH₃)₂ | CH | |
| CO₂CH₃ | H | O | H | HC(OCH₃)₂ | N | |
| CO₂CH₃ | H | O | H | H₃CC(OCH₃)₂ | CH | |
| CO₂CH₃ | H | O | H | H₃CC(OCH₃)₂ | N | |
| CO₂CH₃ | H | O | H | HC(SCH₃)₂ | CH | |
| CO₂CH₃ | H | O | H | HC(SCH₃)₂ | N | |
| CO₂C₃H₇ | H | O | H | CH₃ | CH | |
| CO₂C₃H₇ | H | O | H | CH₃ | N | |
| CO₂CH₂CH=CH₂ | H | O | H | OCH₃ | CH | |

TABLE I-continued

General Formula I

| $R_5$ | $R_6$ | W | R | $R_1$ | Z | m.p. (°C.) |
|---|---|---|---|---|---|---|
| $CO_2CH_2CH=CH_2$ | H | O | H | $OCH_3$ | N | |
| $CO_2CH_2C\equiv CH$ | H | O | H | $CH_3$ | CH | |
| $CO_2CH_2C\equiv CH$ | H | O | H | $CH_3$ | N | |
| $CO_2CH_2C\equiv CH$ | H | O | H | $OCH_3$ | CH | |
| $CO_2CH_2C\equiv CH$ | H | O | H | $OCH_3$ | N | |
| $CO_2CH_2CH_2OCH_3$ | H | O | H | $CH_3$ | CH | |
| $CO_2CH_2CH_2OCH_3$ | H | O | H | $CH_3$ | N | |
| $CO_2CH_2CH_2OCH_3$ | H | O | H | $OCH_3$ | CH | |
| $CO_2CH_2CH_2OCH_3$ | H | O | H | $OCH_3$ | N | |
| $CO_2CH_2CH_2Cl$ | H | O | H | $CH_3$ | CH | |
| $CO_2CH_2CH_2Cl$ | H | O | H | $CH_3$ | N | |
| $CO_2CH_2CH_2Cl$ | H | O | H | $OCH_3$ | CH | |
| $CO_2CH_2CH_2Cl$ | H | O | H | $OCH_3$ | N | |
| $CO_2CH_2CH_2F$ | H | O | H | $CH_3$ | CH | |
| $CO_2CH_2CH_2F$ | H | O | H | $CH_3$ | N | |
| $CO_2CH_2CH_2F$ | H | O | H | $OCH_3$ | CH | |
| $CO_2CH_2CH_2F$ | H | O | H | $OCH_3$ | N | |
| $SO_2N(CH_3)_2$ | H | O | H | $CH_3$ | CH | |
| $SO_2N(CH_3)_2$ | H | O | H | $CH_3$ | N | |
| $SO_2N(CH_3)_2$ | H | S | H | $CH_3$ | CH | |
| $SO_2N(CH_3)_2$ | H | S | H | $CH_3$ | N | |
| $SO_2N(CH_3)_2$ | H | O | $CH_3$ | $CH_3$ | CH | |
| $SO_2N(CH_3)_2$ | H | O | $CH_3$ | $CH_3$ | N | |
| $SO_2N(CH_3)_2$ | 5-Cl | O | H | $CH_3$ | CH | |
| $SO_2N(CH_3)_2$ | 5-Cl | O | H | $CH_3$ | N | |
| $SO_2N(CH_3)_2$ | 5-Br | O | H | $CH_3$ | CH | |
| $SO_2N(CH_3)_2$ | 5-Br | O | H | $CH_3$ | N | |
| $SO_2N(CH_3)_2$ | 5-$OCH_3$ | O | H | $CH_3$ | CH | |
| $SO_2N(CH_3)_2$ | 5-$OCH_3$ | O | H | $CH_3$ | N | |
| $SO_2N(CH_3)_2$ | 5-$CH_3$ | O | H | $CH_3$ | CH | |
| $SO_2N(CH_3)_2$ | 5-$CH_3$ | O | H | $CH_3$ | N | |
| $SO_2N(CH_3)_2$ | 5-CN | O | H | $CH_3$ | CH | |
| $SO_2N(CH_3)_2$ | 5-CN | O | H | $CH_3$ | N | |
| $SO_2N(CH_3)_2$ | 5-$CH_2OCH_3$ | O | H | $CH_3$ | CH | |
| $SO_2N(CH_3)_2$ | 5-$CH_2OCH_3$ | O | H | $CH_3$ | N | |
| $SO_2N(CH_3)_2$ | 5-$OCF_2H$ | O | H | $CH_3$ | CH | |
| $SO_2N(CH_3)_2$ | 5-$OCF_2H$ | O | H | $CH_3$ | N | |
| $SO_2N(CH_3)_2$ | H | O | H | $OCH_3$ | CH | |
| $SO_2N(CH_3)_2$ | H | O | H | $OCH_3$ | N | |
| $SO_2N(CH_3)_2$ | H | S | H | $OCH_3$ | CH | |
| $SO_2N(CH_3)_2$ | H | S | H | $OCH_3$ | N | |
| $SO_2N(CH_3)_2$ | H | O | $CH_3$ | $OCH_3$ | CH | |
| $SO_2N(CH_3)_2$ | H | O | $CH_3$ | $OCH_3$ | N | |
| $SO_2N(CH_3)_2$ | 5-Cl | O | H | $OCH_3$ | CH | |
| $SO_2N(CH_3)_2$ | 5-Cl | O | H | $OCH_3$ | N | |
| $SO_2N(CH_3)_2$ | 5-Br | O | H | $OCH_3$ | CH | |
| $SO_2N(CH_3)_2$ | 5-Br | O | H | $OCH_3$ | N | |
| $SO_2N(CH_3)_2$ | 5-$OCH_3$ | O | H | $OCH_3$ | CH | |
| $SO_2N(CH_3)_2$ | 5-$OCH_3$ | O | H | $OCH_3$ | N | |
| $SO_2N(CH_3)_2$ | 5-$CH_3$ | O | H | $OCH_3$ | CH | |
| $SO_2N(CH_3)_2$ | 5-$CH_3$ | O | H | $OCH_3$ | N | |
| $SO_2N(CH_3)_2$ | 5-CN | O | H | $OCH_3$ | CH | |
| $SO_2N(CH_3)_2$ | 5-CN | O | H | $OCH_3$ | N | |
| $SO_2N(CH_3)_2$ | 5-$CH_2OCH_3$ | O | H | $OCH_3$ | CH | |
| $SO_2N(CH_3)_2$ | 5-$CH_2OCH_3$ | O | H | $OCH_3$ | N | |
| $SO_2N(CH_3)_2$ | 5-$OCF_2H$ | O | H | $OCH_3$ | CH | |
| $SO_2N(CH_3)_2$ | 5-$OCF_2H$ | O | H | $OCH_3$ | N | |
| $SO_2N(CH_3)C_2H_5$ | H | O | H | $OCH_3$ | CH | |
| $SO_2N(CH_3)C_2H_5$ | H | O | H | $OCH_3$ | N | |
| $SO_2N(C_2H_5)_2$ | H | O | H | $OCH_3$ | CH | |
| $SO_2N(C_2H_5)_2$ | H | O | H | $OCH_3$ | N | |
| $SO_2NHCH_3$ | H | O | H | $OCH_3$ | CH | |
| $SO_2NHCH_3$ | H | O | H | $OCH_3$ | N | |
| $SO_2NHC_2H_5$ | H | O | H | $OCH_3$ | CH | |
| $SO_2NHC_2H_5$ | H | O | H | $OCH_3$ | N | |
| $SO_2N(CH_3)_2$ | H | O | H | $OC_2H_5$ | CH | |
| $SO_2N(CH_3)_2$ | H | O | H | $OC_2H_5$ | N | |
| $SO_2N(CH_3)C_2H_5$ | H | O | H | $OC_2H_5$ | CH | |
| $SO_2N(CH_3)C_2H_5$ | H | O | H | $OC_2H_5$ | N | |
| $SO_2NHCH_3$ | H | O | H | $OC_2H_5$ | CH | |
| $SO_2NHCH_3$ | H | O | H | $OC_2H_5$ | N | |
| $SO_2N(CH_3)_2$ | H | O | H | $C_2H_5$ | CH | |
| $SO_2N(CH_3)_2$ | H | O | H | $C_2H_5$ | N | |
| $SO_2N(CH_3)_2$ | H | O | H | $SCH_3$ | CH | |
| $SO_2N(CH_3)_2$ | H | O | H | $SCH_3$ | N | |
| $SO_2N(CH_3)_2$ | H | O | H | $OCH_2CF_3$ | CH | |
| $SO_2N(CH_3)_2$ | H | O | H | $OCH_2CF_3$ | N | |
| $SO_2NHCH_3$ | H | O | H | $SCH_3$ | CH | |
| $SO_2NHCH_3$ | H | O | H | $SCH_3$ | N | |
| $SO_2NHCH_3$ | H | O | H | $OCH_2CF_3$ | CH | |

TABLE I-continued

General Formula I

| R₅ | R₆ | W | R | R₁ | Z | m.p. (°C.) |
|---|---|---|---|---|---|---|
| SO₂NHCH₃ | H | O | H | OCH₂CF₃ | N | |
| SO₂N(CH₃)₂ | H | O | H | CH₂SCH₃ | CH | |
| SO₂N(CH₃)₂ | H | O | H | CH₂SCH₃ | N | |
| SO₂N(CH₃)₂ | H | O | H | Cl | CH | |
| SO₂N(CH₃)₂ | H | O | H | Br | CH | |
| SO₂N(CH₃)₂ | H | O | H | CH₂OCH₃ | CH | |
| SO₂N(CH₃)₂ | H | O | H | CH₂OCH₃ | N | |
| SO₂N(CH₃)₂ | H | O | H | OCH₂OCH₃ | CH | |
| SO₂N(CH₃)₂ | H | O | H | OCH₂OCH₃ | N | |
| SO₂N(CH₃)₂ | H | O | H | NH₂ | CH | |
| SO₂N(CH₃)₂ | H | O | H | NH₂ | N | |
| SO₂N(CH₃)₂ | H | O | H | NHCH₃ | CH | |
| SO₂N(CH₃)₂ | H | O | H | NHCH₃ | N | |
| SO₂N(CH₃)₂ | H | O | H | N(CH₃)₂ | CH | |
| SO₂N(CH₃)₂ | H | O | H | N(CH₃)₂ | N | |
| SO₂N(CH₃)₂ | H | O | H | N(C₂H₅)₂ | CH | |
| SO₂N(CH₃)₂ | H | O | H | N(C₂H₅)₂ | N | |
| SO₂N(CH₃)₂ | H | O | H | OCH₂CH=CH₂ | CH | |
| SO₂N(CH₃)₂ | H | O | H | OCH₂CH=CH₂ | N | |
| SO₂N(CH₃)₂ | H | O | H | OCH₂C≡CH | CH | |
| SO₂N(CH₃)₂ | H | O | H | OCH₂C≡CH | N | |
| SO₂N(CH₃)₂ | H | O | H | cyclopropyl | CH | |
| SO₂N(CH₃)₂ | H | O | H | cyclopropyl | N | |
| SO₂N(CH₃)₂ | H | O | H | C≡CH | CH | |
| SO₂N(CH₃)₂ | H | O | H | C≡CH | N | |
| SO₂N(CH₃)₂ | H | O | H | C(O)H | CH | |
| SO₂N(CH₃)₂ | H | O | H | C(O)H | N | |
| SO₂N(CH₃)₂ | H | O | H | C(O)CH₃ | CH | |
| SO₂N(CH₃)₂ | H | O | H | C(O)CH₃ | N | |
| SO₂N(CH₃)₂ | H | O | H | N(OCH₃)CH₃ | CH | |
| SO₂N(CH₃)₂ | H | O | H | N(OCH₃)CH₃ | N | |
| SO₂N(CH₃)₂ | H | O | H | HC(OCH₃)₂ | CH | |
| SO₂N(CH₃)₂ | H | O | H | HC(OCH₃)₂ | N | |
| SO₂N(CH₃)₂ | H | O | H | C(OCH₃)₂(CH₃) | CH | |
| SO₂N(CH₃)₂ | H | O | H | C(OCH₃)₂(CH₃) | N | |
| SO₂N(CH₃)₂ | H | O | H | HC(SCH₃)₂ | CH | |
| SO₂N(CH₃)₂ | H | O | H | HC(SCH₃)₂ | N | |
| OSO₂CH₃ | H | O | H | CH₃ | CH | |
| OSO₂CH₃ | H | O | H | CH₃ | N | |
| OSO₂C₂H₅ | H | O | H | CH₃ | CH | |
| OSO₂C₂H₅ | H | O | H | CH₃ | N | |
| OSO₂N(CH₃)₂ | H | O | H | CH₃ | CH | |
| OSO₂N(CH₃)₂ | H | O | H | CH₃ | N | |
| OSO₂CH₃ | H | O | CH₃ | CH₃ | CH | |
| OSO₂CH₃ | H | O | CH₃ | CH₃ | N | |
| OSO₂CH₃ | H | S | H | CH₃ | CH | |
| OSO₂CH₃ | H | S | H | CH₃ | N | |
| OSO₂CH₃ | H | O | H | OCH₃ | CH | |
| OSO₂CH₃ | H | O | H | OCH₃ | N | |
| OSO₂CH₃ | H | O | CH₃ | OCH₃ | CH | |
| OSO₂CH₃ | H | O | CH₃ | OCH₃ | N | |
| OSO₂N(CH₃)₂ | H | O | H | OCH₃ | CH | |
| OSO₂N(CH₃)₂ | H | O | H | OCH₃ | N | |
| OSO₂C₂H₅ | H | O | H | OCH₃ | CH | |
| OSO₂C₂H₅ | H | O | H | OCH₃ | N | |
| OSO₂CH₃ | H | O | H | OC₂H₅ | CH | |
| OSO₂CH₃ | H | O | H | OC₂H₅ | N | |
| OSO₂CH₃ | H | O | H | C₂H₅ | CH | |
| OSO₂CH₃ | H | O | H | C₂H₅ | N | |
| OSO₂CH₃ | H | O | H | SCH₃ | CH | |
| OSO₂CH₃ | H | O | H | SCH₃ | N | |
| OSO₂CH₃ | H | O | H | OCH₂CF₃ | CH | |
| OSO₂CH₃ | H | O | H | OCH₂CF₃ | N | |
| OSO₂CH₃ | H | O | H | CH₂SCH₃ | CH | |
| OSO₂CH₃ | H | O | H | CH₂SCH₃ | N | |
| OSO₂CH₃ | H | O | H | Cl | CH | |
| SO₂CH₃ | H | O | H | CH₃ | CH | |
| SO₂CH₃ | H | O | H | CH₃ | N | |
| SO₂C₂H₅ | H | O | H | CH₃ | CH | |
| SO₂C₂H₅ | H | O | H | CH₃ | N | |
| SO₂CH₂CH=CH₂ | H | O | H | CH₃ | CH | |
| SO₂CH₂CH=CH₂ | H | O | H | CH₃ | N | |
| SO₂CH₂≡CH | H | O | H | CH₃ | CH | |
| SO₂CH₂≡CH | H | O | H | CH₃ | N | |
| SO₂CH₂CF₃ | H | O | H | CH₃ | CH | |
| SO₂CH₂CF₃ | H | O | H | CH₃ | N | |
| SO₂CH₃ | 5-Cl | O | H | CH₃ | CH | |
| SO₂CH₃ | 5-Cl | O | H | CH₃ | N | |
| SO₂CH₃ | 5-Br | O | H | CH₃ | CH | |
| SO₂CH₃ | 5-Br | O | H | CH₃ | N | |

TABLE I-continued

General Formula I

| $R_5$ | $R_6$ | W | R | $R_1$ | Z | m.p. (°C.) |
|---|---|---|---|---|---|---|
| $SO_2CH_3$ | 5-$OCH_3$ | O | H | $CH_3$ | CH | |
| $SO_2CH_3$ | 5-$OCH_3$ | O | H | $CH_3$ | N | |
| $SO_2CH_3$ | 5-$CH_3$ | O | H | $CH_3$ | CH | |
| $SO_2CH_3$ | 5-$CH_3$ | O | H | $CH_3$ | N | |
| $SO_2CH_3$ | 5-CN | O | H | $CH_3$ | CH | |
| $SO_2CH_3$ | 5-CN | O | H | $CH_3$ | N | |
| $SO_2CH_3$ | 5-$OCF_2H$ | O | H | $CH_3$ | CH | |
| $SO_2CH_3$ | 5-$OCF_2H$ | O | H | $CH_3$ | N | |
| $SO_2CH_3$ | H | O | H | $OCH_3$ | CH | |
| $SO_2CH_3$ | H | O | H | $OCH_3$ | N | |
| $SO_2CH_3$ | H | O | $CH_3$ | $OCH_3$ | CH | |
| $SO_2CH_3$ | H | O | $CH_3$ | $OCH_3$ | N | |
| $SO_2CH_3$ | 5-Cl | O | H | $OCH_3$ | CH | |
| $SO_2CH_3$ | 5-Cl | O | H | $OCH_3$ | N | |
| $SO_2CH_3$ | 5-Br | O | H | $OCH_3$ | CH | |
| $SO_2CH_3$ | 5-Br | O | H | $OCH_3$ | N | |
| $SO_2CH_3$ | 5-$OCH_3$ | O | H | $OCH_3$ | CH | |
| $SO_2CH_3$ | 5-$OCH_3$ | O | H | $OCH_3$ | N | |
| $SO_2CH_3$ | 5-$CH_3$ | O | H | $OCH_3$ | CH | |
| $SO_2CH_3$ | 5-$CH_3$ | O | H | $OCH_3$ | N | |
| $SO_2CH_3$ | 5-CN | O | H | $OCH_3$ | CH | |
| $SO_2CH_3$ | 5-CN | O | H | $OCH_3$ | N | |
| $SO_2CH_3$ | 5-$OCF_2H$ | O | H | $OCH_3$ | CH | |
| $SO_2CH_3$ | 5-$OCF_2H$ | O | H | $OCH_3$ | N | |
| $SO_2CH_2C\equiv CH$ | H | O | H | $OCH_3$ | CH | |
| $SO_2CH_2C\equiv CH$ | H | O | H | $OCH_3$ | N | |
| $SO_2CH_2CF_3$ | H | O | H | $OCH_3$ | CH | |
| $SO_2CH_2CF_3$ | H | O | H | $OCH_3$ | N | |
| C(O)H | H | O | H | $CH_3$ | CH | |
| C(O)H | H | O | H | $CH_3$ | N | |
| C(O)H | H | O | H | $OCH_3$ | CH | |
| C(O)H | H | O | H | $OCH_3$ | N | |
| $COCH_3$ | H | O | H | $CH_3$ | CH | |
| $COCH_3$ | H | O | H | $CH_3$ | N | |
| $COCH_3$ | H | O | H | $OCH_3$ | CH | |
| $COCH_3$ | H | O | H | $OCH_3$ | N | |
| $COC_2H_5$ | H | O | H | $CH_3$ | CH | |
| $COC_2H_5$ | H | O | H | $CH_3$ | N | |
| $COC_2H_5$ | H | O | H | $CH_3$ | CH | |
| $COC_2H_5$ | H | O | H | $OCH_3$ | N | |
| $COC_2H_5$ | H | O | H | $OCH_3$ | N | |
| $COCH_2CH=CH_2$ | H | O | H | $CH_3$ | CH | |
| $COCH_2CH=CH_2$ | H | O | H | $CH_3$ | N | |
| $COCH_2CH=CH_2$ | H | O | H | $OCH_3$ | CH | |
| $COCH_2CH=CH_2$ | H | O | H | $OCH_3$ | N | |
| $COCH_2C\equiv CH$ | H | O | H | $CH_3$ | CH | |
| $COCH_2C\equiv CH$ | H | O | H | $CH_3$ | N | |
| $COCH_2C\equiv CH$ | H | O | H | $OCH_3$ | CH | |
| $COCH_2C\equiv CH$ | H | O | H | $OCH_3$ | N | |
| $COCH_2CH_2F$ | H | O | H | $CH_3$ | CH | |
| $COCH_2CH_2F$ | H | O | H | $CH_3$ | N | |
| $COCH_2CH_2F$ | H | O | H | $OCH_3$ | CH | |
| $COCH_2CH_2F$ | H | O | H | $OCH_3$ | N | |
| $COCH_2CF_3$ | H | O | H | $CH_3$ | CH | |
| $COCH_2CF_3$ | H | O | H | $CH_3$ | N | |
| $COCH_2CF_3$ | H | O | H | $OCH_3$ | CH | |
| $COCH_2CF_3$ | H | O | H | $OCH_3$ | N | |
| $COCH_3$ | 5-Cl | O | H | $OCH_3$ | CH | |
| $COCH_3$ | 5-Cl | O | H | $OCH_3$ | N | |
| $COCH_3$ | 5-Br | O | H | $OCH_3$ | CH | |
| $COCH_3$ | 5-Br | O | H | $OCH_3$ | N | |
| $COCH_3$ | 5-$OCH_3$ | O | H | $OCH_3$ | CH | |
| $COCH_3$ | 5-OCH | O | H | $OCH_3$ | N | |
| $COCH_3$ | 5-$CH_3$ | O | H | $OCH_3$ | CH | |
| $COCH_3$ | 5-$CH_3$ | O | H | $OCH_3$ | N | |
| $COCH_3$ | 5-CN | O | H | $OCH_3$ | CH | |
| $COCH_3$ | 5-CN | O | H | $OCH_3$ | N | |
| $COCH_3$ | 5-$OCF_2H$ | O | H | $OCH_3$ | CH | |
| $COCH_3$ | 5-$OCF_2H$ | O | H | $OCH_3$ | N | |
| $COCH_2OCH_3$ | H | O | H | $CH_3$ | CH | |
| $COCH_2OCH_3$ | H | O | H | $CH_3$ | N | |
| $COCH_2OCH_3$ | H | O | H | $OCH_3$ | CH | |
| $COCH_2OCH_3$ | H | O | H | $OCH_3$ | N | |
| Cl | H | O | H | $CH_3$ | CH | |
| Cl | H | O | H | $CH_3$ | N | |
| Cl | H | O | H | $OCH_3$ | CH | |
| Cl | H | O | H | $OCH_3$ | N | |
| Br | H | O | H | $CH_3$ | CH | |
| Br | H | O | H | $CH_3$ | N | |
| Br | H | O | H | $OCH_3$ | CH | |

TABLE I-continued

General Formula I

| $R_5$ | $R_6$ | W | R | $R_1$ | Z | m.p. (°C.) |
|---|---|---|---|---|---|---|
| Br | H | O | H | $OCH_3$ | N | |
| Br | H | O | $CH_3$ | $OCH_3$ | CH | |
| Br | H | O | $CH_3$ | $OCH_3$ | N | |
| $NO_2$ | H | O | H | $CH_3$ | CH | |
| $NO_2$ | H | O | H | $CH_3$ | N | |
| $NO_2$ | H | O | H | $OCH_3$ | CH | |
| $NO_2$ | H | O | H | $OCH_3$ | N | |
| $CH_3$ | H | O | H | $CH_3$ | CH | |
| $CH_3$ | H | O | H | $CH_3$ | N | |
| $CH_3$ | H | O | H | $OCH_3$ | CH | |
| $CH_3$ | H | O | H | $OCH_3$ | N | |
| $C_2H_5$ | H | O | H | $CH_3$ | CH | |
| $C_2H_5$ | H | O | H | $CH_3$ | N | |
| $C_2H_5$ | H | O | H | $OCH_3$ | CH | |
| $C_2H_5$ | H | O | H | $OCH_3$ | N | |
| $CH_2CH=CH_2$ | H | O | H | $CH_3$ | CH | |
| $CH_2CH=CH_2$ | H | O | H | $CH_3$ | N | |
| $CH_2CH=CH_2$ | H | O | H | $OCH_3$ | CH | |
| $CH_2CH=CH_2$ | H | O | H | $OCH_3$ | N | |
| $CH_2C\equiv CH$ | H | O | H | $CH_3$ | CH | |
| $CH_2C\equiv CH$ | H | O | H | $CH_3$ | N | |
| $CH_2C\equiv CH$ | H | O | H | $OCH_3$ | CH | |
| $CH_2C\equiv CH$ | H | O | H | $OCH_3$ | N | |
| $CF_3$ | H | O | H | $CH_3$ | CH | |
| $CF_3$ | H | O | H | $CH_3$ | N | |
| $CF_3$ | H | O | H | $OCH_3$ | CH | |
| $CF_3$ | H | O | H | $OCH_3$ | N | |
| $CH_2CF_3$ | H | O | H | $CH_3$ | CH | |
| $CH_2CF_3$ | H | O | H | $OCH_3$ | N | |
| $CH_2CF_3$ | H | O | H | $CH_3$ | CH | |
| $CH_2CF_3$ | H | O | H | $OCH_3$ | N | |
| $OCH_3$ | H | O | H | $CH_3$ | CH | |
| $OCH_3$ | H | O | H | $CH_3$ | N | |
| $OCH_3$ | H | O | H | $OCH_3$ | CH | |
| $OCH_3$ | H | O | H | $OCH_3$ | N | |
| $OC_3H_7$ | H | O | H | $CH_3$ | CH | |
| $OC_3H_7$ | H | O | H | $CH_3$ | N | |
| $OC_3H_7$ | H | O | H | $OCH_3$ | CH | |
| $OC_3H_7$ | H | O | H | $OCH_3$ | N | |
| $OCH_2CH_2OCH_3$ | H | O | H | $CH_3$ | CH | |
| $OCH_2CH_2OCH_3$ | H | O | H | $CH_3$ | N | |
| $OCH_2CH_2OCH_3$ | H | O | H | $OCH_3$ | CH | |
| $OCH_2CH_2OCH_3$ | H | O | H | $OCH_3$ | N | |
| $OCF_2H$ | H | O | H | $CH_3$ | CH | |
| $OCF_2H$ | H | O | H | $CH_3$ | N | |
| $OCF_2H$ | H | O | H | $OCH_3$ | CH | |
| $OCF_2H$ | H | O | H | $OCH_3$ | N | |
| $OCH_2CH=CH_2$ | H | O | H | $CH_3$ | CH | |
| $OCH_2CH=CH_2$ | H | O | H | $CH_3$ | N | |
| $OCH_2CH=CH_2$ | H | O | H | $OCH_3$ | CH | |
| $OCH_2CH=CH_2$ | H | O | H | $OCH_3$ | N | |
| $OCH_2C\equiv CH$ | H | O | H | $CH_3$ | CH | |
| $OCH_2C\equiv CH$ | H | O | H | $OCH_3$ | N | |
| $OCH_2C\equiv CH$ | H | O | H | $CH_3$ | CH | |
| $OCH_2C\equiv CH$ | H | O | H | $OCH_3$ | N | |
| $CONHCH_3$ | H | O | H | $CH_3$ | CH | |
| $CONHCH_3$ | H | O | H | $CH_3$ | N | |
| $CONHCH_3$ | H | O | H | $OCH_3$ | CH | |
| $CONHCH_3$ | H | O | H | $OCH_3$ | N | |
| $CON(CH_3)_2$ | H | O | H | $CH_3$ | CH | |
| $CON(CH_3)_2$ | H | O | H | $CH_3$ | N | |
| $CON(CH_3)_2$ | H | O | H | $OCH_3$ | CH | |
| $CON(CH_3)_2$ | H | O | H | $OCH_3$ | N | |
| $CON(CH_3)C_2H_5$ | H | O | H | $CH_3$ | CH | |
| $CON(CH_3)C_2H_5$ | H | O | H | $CH_3$ | N | |
| $CON(CH_3)C_2H_5$ | H | O | H | $OCH_3$ | CH | |
| $CON(CH_3)C_2H_5$ | H | O | H | $OCH_3$ | N | |
| $SO_2N(OCH_3)CH_3$ | H | O | H | $CH_3$ | CH | |
| $SO_2N(OCH_3)CH_3$ | H | O | H | $CH_3$ | N | |
| $SO_2N(OCH_3)CH_3$ | H | O | H | $OCH_3$ | CH | |
| $SO_2N(OCH_3)CH_3$ | H | O | H | $OCH_3$ | N | |
| $CH_2OCH_3$ | H | O | H | $CH_3$ | CH | |
| $CH_2OCH_3$ | H | O | H | $CH_3$ | N | |
| $CH_2OCH_3$ | H | O | H | $OCH_3$ | CH | |
| $CH_2OCH_3$ | H | O | H | $OCH_3$ | N | |
| $CH_2CN$ | H | O | H | $CH_3$ | CH | |
| $CH_2CN$ | H | O | H | $CH_3$ | N | |
| $CH_2CN$ | H | O | H | $OCH_3$ | CH | |
| $CH_2CN$ | H | O | H | $OCH_3$ | N | |
| $C_6H_5$ | H | O | H | $CH_3$ | CH | |

TABLE I-continued

General Formula I

| R$_5$ | R$_6$ | W | R | R$_1$ | Z | m.p. (°C.) |
|---|---|---|---|---|---|---|
| C$_6$H$_5$ | H | O | H | CH$_3$ | N | |
| C$_6$H$_5$ | H | O | H | OCH$_3$ | CH | |
| C$_6$H$_5$ | H | O | H | OCH$_3$ | N | |
| HC(OCH$_3$)$_2$ | H | O | H | CH$_3$ | CH | |
| HC(OCH$_3$)$_2$ | H | O | H | CH$_3$ | N | |
| HC(OCH$_3$)$_2$ | H | O | H | OCH$_3$ | CH | |
| HC(OCH$_3$)$_2$ | H | O | H | OCH$_3$ | N | |
| H$_3$CC(OCH$_3$)$_2$ | H | O | H | CH$_3$ | CH | |
| H$_3$CC(OCH$_3$)$_2$ | H | O | H | CH$_3$ | N | |
| H$_3$CC(OCH$_3$)$_2$ | H | O | H | OCH$_3$ | CH | |
| H$_3$CC(OCH$_3$)$_2$ | H | O | H | OCH$_3$ | N | |
| Q-1 | H | O | H | CH$_3$ | CH | |
| Q-1 | H | O | H | OCH$_3$ | CH | |
| Q-2 | H | O | H | CH$_3$ | CH | |
| Q-2 | H | O | H | OCH$_3$ | CH | |
| Q-3 | H | O | H | CH$_3$ | CH | |
| Q-3 | H | O | H | OCH$_3$ | CH | |
| Q-4 | H | O | H | CH$_3$ | CH | |
| Q-4 | H | O | H | OCH$_3$ | CH | |
| Q-5 | H | O | H | CH$_3$ | CH | |
| Q-5 | H | O | H | OCH$_3$ | CH | |
| Q-6 | H | O | H | CH$_3$ | CH | |
| Q-6 | H | O | H | OCH$_3$ | CH | |
| Q-7 | H | O | H | CH$_3$ | CH | |
| Q-7 | H | O | H | OCH$_3$ | CH | |
| Q-8 | H | O | H | CH$_3$ | CH | |
| Q-8 | H | O | H | OCH$_3$ | CH | |
| Q-9 | H | O | H | CH$_3$ | CH | |
| Q-9 | H | O | H | OCH$_3$ | CH | |
| Q-10 | H | O | H | CH$_3$ | CH | |
| Q-10 | H | O | H | OCH$_3$ | CH | |
| Q-11 | H | O | H | CH$_3$ | CH | |
| Q-11 | H | O | H | OCH$_3$ | CH | |
| Q-12 | H | O | H | CH$_3$ | CH | |
| Q-12 | H | O | H | OCH$_3$ | CH | |
| Q-13 | H | O | H | CH$_3$ | CH | |
| Q-13 | H | O | H | OCH$_3$ | CH | |
| Q-14(R$_{22}$=H) | H | O | H | CH$_3$ | CH | |
| Q-14(R$_{22}$=CH$_3$) | H | O | H | OCH$_3$ | CH | |
| Q-15 | H | O | H | CH$_3$ | CH | |
| Q-15 | H | O | H | OCH$_3$ | CH | |
| Q-16 | H | O | H | CH$_3$ | CH | |
| Q-16 | H | O | H | OCH$_3$ | CH | |
| Q-17 | H | O | H | CH$_3$ | CH | |
| Q-17 | H | O | H | OCH$_3$ | CH | |
| Q-18 | H | O | H | CH$_3$ | CH | |
| Q-18 | H | O | H | OCH$_3$ | CH | |
| Q-19 | H | O | H | CH$_3$ | CH | |
| Q-19 | H | O | H | OCH$_3$ | CH | |
| Q-20(R$_{22}$=H) | H | O | H | CH$_3$ | CH | |
| Q-20(R$_{22}$=CH$_3$) | H | O | H | OCH$_3$ | CH | |

TABLE II

General Formula II

| R$_5$ | R$_6$ | R | X | m.p. (°C.) |
|---|---|---|---|---|
| CO$_2$CH$_3$ | H | H | O | |
| CO$_2$CH$_3$ | H | H | CH$_2$ | |
| CO$_2$CH$_3$ | H | CH$_3$ | O | |
| CO$_2$CH$_3$ | H | CH$_3$ | CH$_2$ | |
| SO$_2$N(CH$_3$)$_2$ | H | H | O | |
| SO$_2$N(CH$_3$)$_2$ | H | H | CH$_2$ | |
| SO$_2$N(CH$_3$)$_2$ | H | CH$_3$ | O | |
| SO$_2$N(CH$_3$)$_2$ | H | CH$_3$ | CH$_2$ | |

TABLE III

General Formula III

| R$_5$ | R$_6$ | W | R | m.p. (°C.) |
|---|---|---|---|---|
| CO$_2$CH$_3$ | H | O | H | |
| CO$_2$CH$_3$ | H | O | CH$_3$ | |
| CO$_2$CH$_3$ | H | S | H | |
| SO$_2$N(CH$_3$)$_2$ | H | O | H | |
| SO$_2$N(CH$_3$)$_2$ | H | O | CH$_3$ | |
| SO$_2$N(CH$_3$)$_2$ | H | S | H | |
| SO$_2$CH$_3$ | H | O | H | |
| SO$_2$CH$_3$ | H | O | CH$_3$ | |

TABLE IV

General Formula IV

| R$_5$ | R$_6$ | R | Y | m.p. (°C.) |
|---|---|---|---|---|
| CO$_2$CH$_3$ | H | H | H | |
| CO$_2$CH$_3$ | H | H | CH$_3$ | |
| CO$_2$CH$_3$ | H | CH$_3$ | H | |
| CO$_2$CH$_3$ | H | CH$_3$ | CH$_3$ | |
| SO$_2$N(CH$_3$)$_2$ | H | H | H | |
| SO$_2$N(CH$_3$)$_2$ | H | H | CH$_3$ | |
| SO$_2$N(CH$_3$)$_2$ | H | CH$_3$ | H | |
| SO$_2$N(CH$_3$)$_2$ | H | CH$_3$ | CH$_3$ | |
| SO$_2$CH$_3$ | H | H | H | |
| SO$_2$CH$_3$ | H | H | CH$_3$ | |
| SO$_2$CH$_3$ | H | CH$_3$ | H | |
| SO$_2$CH$_3$ | H | CH$_3$ | CH$_3$ | |

TABLE V

General Formula V

| $R_5$ | $R_6$ | R | $R_1$ | m.p. (°C.) |
|---|---|---|---|---|
| $CO_2CH_3$ | H | H | H | |
| $CO_2CH_3$ | H | H | $CH_3$ | |
| $CO_2CH_3$ | H | H | $CH_2CH_3$ | |
| $CO_2CH_3$ | H | H | $CH_2CF_3$ | |
| $CO_2CH_3$ | H | $CH_3$ | H | |
| $SO_2N(CH_3)_2$ | H | H | H | |
| $SO_2N(CH_3)_2$ | H | H | $CH_3$ | |
| $SO_2N(CH_3)_2$ | H | H | $CH_2CH_3$ | |
| $SO_2N(CH_3)_2$ | H | H | $CH_2CF_3$ | |
| $SO_2N(CH_3)_2$ | H | $CH_3$ | H | |
| $SO_2CH_3$ | H | H | $CH_3$ | |
| $SO_2CH_3$ | H | H | $CH_2CH_3$ | |
| $SO_2CH_3$ | H | H | $CH_2CF_3$ | |
| $SO_2CH_3$ | H | H | H | |
| $SO_2CH_3$ | H | $CH_3$ | $CH_3$ | |

TABLE VI

General Formula VI

| $R_7$ | $R_1$ | Z | m.p. (°C.) |
|---|---|---|---|
| Cl | $CH_3$ | CH | |
| Cl | $CH_3$ | N | |
| Cl | $OCH_3$ | CH | |
| Cl | $OCH_3$ | N | |
| Cl | $N(CH_3)_2$ | CH | |
| Cl | $N(CH_3)_2$ | N | |
| $CO_2CH_3$ | $CH_3$ | CH | |
| $CO_2CH_3$ | $CH_3$ | N | |
| $CO_2CH_3$ | $OCH_3$ | CH | |
| $CO_2CH_3$ | $OCH_3$ | N | |
| $CO_2CH_3$ | $N(CH_3)_2$ | CH | |
| $CO_2CH_3$ | $N(CH_3)_2$ | N | |
| $SO_2N(CH_3)_2$ | $CH_3$ | CH | |
| $SO_2N(CH_3)_2$ | $CH_3$ | N | |
| $SO_2N(CH_3)_2$ | $OCH_3$ | CH | |
| $SO_2N(CH_3)_2$ | $OCH_3$ | N | |
| $SO_2N(CH_3)_2$ | $N(CH_3)_2$ | CH | |
| $SO_2N(CH_3)_2$ | $N(CH_3)_2$ | N | |
| $OSO_2CH_3$ | $CH_3$ | CH | |
| $OSO_2CH_3$ | $CH_3$ | N | |
| $OSO_2CH_3$ | $OCH_3$ | CH | |
| $OSO_2CH_3$ | $OCH_3$ | N | |
| $OSO_2CH_3$ | $N(CH_3)_2$ | CH | |
| $OSO_2CH_3$ | $N(CH_3)_2$ | N | |
| $SO_2CH_3$ | $CH_3$ | CH | |
| $SO_2CH_3$ | $CH_3$ | N | |
| $SO_2CH_3$ | $OCH_3$ | CH | |
| $SO_2CH_3$ | $OCH_3$ | N | |
| $SO_2CH_3$ | $N(CH_3)_2$ | CH | |
| $SO_2CH_3$ | $N(CH_3)_2$ | N | |

TABLE VII

General Formula VII

| $R_8$ | $R_9$ | $R_1$ | Z | m.p. (°C.) |
|---|---|---|---|---|
| $CH_3$ | H | $CH_3$ | CH | |
| $CH_3$ | H | $CH_3$ | N | |
| $CH_3$ | H | $OCH_3$ | CH | |
| $CH_3$ | H | $OCH_3$ | N | |
| $CH_3$ | 5-$CH_3$ | $OCH_3$ | CH | |
| $CH_3$ | 5-$CH_3$ | $OCH_3$ | N | |
| $OCH_3$ | H | $CH_3$ | CH | |
| $OCH_3$ | H | $CH_3$ | N | |
| $OCH_3$ | H | $OCH_3$ | CH | |
| $OCH_3$ | H | $OCH_3$ | N | |
| $OCH_3$ | 4-$CH_3$ | $OCH_3$ | CH | |
| $OCH_3$ | 4-$CH_3$ | $OCH_3$ | N | |
| Cl | H | $CH_3$ | CH | |
| Cl | H | $CH_3$ | N | |
| Cl | H | $OCH_3$ | CH | |
| Cl | H | $OCH_3$ | N | |
| Cl | 5-$CH_3$ | $OCH_3$ | CH | |
| Cl | 5-$CH_3$ | $OCH_3$ | N | |
| $CO_2CH_3$ | H | $CH_3$ | CH | |
| $CO_2CH_3$ | H | $CH_3$ | N | |
| $CO_2CH_3$ | H | $OCH_3$ | CH | |
| $CO_2CH_3$ | H | $OCH_3$ | N | |
| $CO_2CH_3$ | 5-$CH_3$ | $OCH_3$ | CH | |
| $CO_2CH_3$ | 4-$CH_3$ | $OCH_3$ | N | |
| $SO_2N(CH_3)_2$ | H | $CH_3$ | CH | |
| $SO_2N(CH_3)_2$ | H | $CH_3$ | N | |
| $SO_2N(CH_3)_2$ | H | $OCH_3$ | CH | |
| $SO_2N(CH_3)_2$ | H | $OCH_3$ | N | |
| $SO_2N(CH_3)_2$ | 4-$CH_3$ | $OCH_3$ | N | |
| $SO_2N(CH_3)_2$ | 5-$CH_3$ | $OCH_3$ | CH | |
| CF=CFCl | H | $CH_3$ | CH | |
| CF=CFCl | H | $CH_3$ | N | |
| CF=CFCl | H | $OCH_3$ | CH | |
| CF=CFCl | H | $OCH_3$ | N | |
| CF=CFCl | 4-$CH_3$ | $OCH_3$ | CH | |
| CF=CFCl | 4-$CH_3$ | $OCH_3$ | CH | |
| CF=CFCF_3 | H | $CH_3$ | CH | |
| CF=CFCF_3 | H | $CH_3$ | N | |
| CF=CFCF_3 | H | $OCH_3$ | CH | |
| CF=CFCF_3 | H | $OCH_3$ | N | |
| CF=CFCF_3 | 5-$CH_3$ | $OCH_3$ | N | |
| CF=CFCF_3 | 5-$CH_3$ | $OCH_3$ | CH | |

TABLE VIII

General Formula VIII

| $R_8$ | $R_9$ | $R_1$ | Z | m.p. (°C.) |
|---|---|---|---|---|
| $CH_3$ | H | $CH_3$ | CH | |
| $CH_3$ | H | $CH_3$ | N | |
| $CH_3$ | H | $OCH_3$ | CH | |
| $CH_3$ | H | $OCH_3$ | N | |
| $CH_3$ | 4-$CH_3$ | $OCH_3$ | CH | |
| $CH_3$ | 4-$CH_3$ | $OCH_3$ | N | |
| $OCH_3$ | H | $CH_3$ | CH | |
| $OCH_3$ | H | $CH_3$ | N | |
| $OCH_3$ | H | $OCH_3$ | CH | |
| $OCH_3$ | H | $OCH_3$ | N | |
| $OCH_3$ | 5-$CH_3$ | $OCH_3$ | CH | |
| $OCH_3$ | 5-$CH_3$ | $OCH_3$ | N | |
| Cl | H | $CH_3$ | CH | |
| Cl | H | $CH_3$ | N | |
| Cl | H | $OCH_3$ | CH | |
| Cl | H | $OCH_3$ | N | |
| Cl | 4-$CH_3$ | $OCH_3$ | CH | |
| Cl | 4-$CH_3$ | $OCH_3$ | N | |
| $CO_2CH_3$ | H | $CH_3$ | CH | |
| $CO_2CH_3$ | H | $CH_3$ | N | |
| $CO_2CH_3$ | H | $OCH_3$ | CH | 89–92 |
| $CO_2CH_3$ | H | $OCH_3$ | N | |
| $CO_2CH_3$ | 5-$CH_3$ | $OCH_3$ | CH | |
| $CO_2CH_3$ | 5-$CH_3$ | $OCH_3$ | N | |
| $SO_2N(CH_3)_2$ | H | $CH_3$ | CH | |
| $SO_2N(CH_3)_2$ | H | $CH_3$ | N | |
| $SO_2N(CH_3)_2$ | H | $OCH_3$ | CH | |
| $SO_2N(CH_3)_2$ | H | $OCH_3$ | N | |
| $SO_2N(CH_3)_2$ | 4-$CH_3$ | $OCH_3$ | CH | |
| $SO_2N(CH_3)_2$ | 4-$CH_3$ | $OCH_3$ | N | |
| CF=CFCl | H | $CH_3$ | CH | |
| CF=CFCl | H | $CH_3$ | N | |
| CF=CFCl | H | $OCH_3$ | CH | |
| CF=CFCl | H | $OCH_3$ | N | |
| CF=CFCl | 4-$CH_3$ | $OCH_3$ | N | |
| CF=CFCl | 4-$CH_3$ | $OCH_3$ | CH | |
| CF=CFCF_3 | H | $CH_3$ | CH | |
| CF=CFCF_3 | H | $CH_3$ | N | |
| CF=CFCF_3 | H | $OCH_3$ | CH | |
| CF=CFCF_3 | H | $OCH_3$ | N | |
| CF=CFCF_3 | 5-$CH_3$ | $OCH_3$ | N | |
| CF=CFCF_3 | 5-$CH_3$ | $OCH_3$ | CH | |

TABLE IX

General Formula IX

| $R_8$ | $R_9$ | $R_1$ | Z | m.p. (°C.) |
|---|---|---|---|---|
| $CH_3$ | H | $CH_3$ | CH | |
| $CH_3$ | H | $CH_3$ | N | |
| $CH_3$ | H | $OCH_3$ | CH | |

TABLE IX-continued

General Formula IX

| R₈ | R₉ | R₁ | Z | m.p. (°C.) |
|---|---|---|---|---|
| CH₃ | H | OCH₃ | N | |
| CH₃ | 2-CH₃ | OCH₃ | CH | |
| CH₃ | 2-CH₃ | OCH₃ | N | |
| OCH₃ | H | CH₃ | CH | |
| OCH₃ | H | CH₃ | N | |
| OCH₃ | H | OCH₃ | CH | |
| OCH₃ | H | OCH₃ | N | |
| OCH₃ | 2-CH₃ | OCH₃ | CH | |
| OCH₃ | 2-CH₃ | OCH₃ | N | |
| Cl | H | CH₃ | CH | |
| CL | H | CH₃ | N | |
| Cl | H | OCH₃ | CH | |
| Cl | H | OCH₃ | N | |
| Cl | 5-CH₃ | OCH₃ | CH | |
| Cl | 5-CH₃ | OCH₃ | N | |
| CO₂CH₃ | H | CH₃ | CH | |
| CO₂CH₃ | H | CH₃ | N | |
| CO₂CH₃ | H | OCH₃ | CH | |
| CO₂CH₃ | H | OCH₃ | N | |
| CO₂CH₃ | 2-CH₃ | OCH₃ | CH | |
| CO₂CH₃ | 2-CH₃ | OCH₃ | N | |
| SO₂N(CH₃)₂ | H | CH₃ | CH | |
| SO₂N(CH₃)₂ | H | CH₃ | N | |
| SO₂N(CH₃)₂ | H | OCH₃ | CH | |
| SO₂N(CH₃)₂ | H | OCH₃ | N | |
| SO₂N(CH₃)₂ | 2-CH₃ | OCH₃ | CH | |
| SO₂N(CH₃)₂ | 2-CH₃ | OCH₃ | N | |
| CF=CFCl | H | CH₃ | CH | |
| CF=CFCl | H | CH₃ | N | |
| CF=CFCl | H | OCH₃ | CH | |
| CF=CFCl | H | OCH₃ | N | |
| CF=CFCl | 2-CH₃ | OCH₃ | CH | |
| CF=CFCl | 2-CH₃ | OCH₃ | N | |
| CF=CFCF₃ | H | CH₃ | CH | |
| CF=CFCF₃ | H | CH₃ | N | |
| CF=CFCF₃ | H | OCH₃ | CH | |
| CF=CFCF₃ | H | OCH₃ | N | |
| CF=CFCF₃ | 5-CH₃ | OCH₃ | CH | |
| CF=CFCF₃ | 5-CH₃ | OCH₃ | N | |

TABLE X

General Formula X

| J | R₁₀ | R₁₀' | R₁₁ | R₁₂ | R₁₃ | R₁ | Z | m.p. (°C.) |
|---|---|---|---|---|---|---|---|---|
| J-6 | COOCH₃ | H | — | — | — | CH₃ | CH | |
| J-6 | COOCH₃ | F | — | — | — | OCH₃ | N | |
| J-6 | COOCH₃ | Cl | — | — | — | CH₃ | CH | |
| J-6 | COOCH₃ | CH₃ | — | — | — | OCH₃ | N | |
| J-6 | COOCH₂CH₃ | H | — | — | — | CH₃ | CH | |
| J-6 | COOCH₂CH₃ | F | — | — | — | CH₃ | CH | |
| J-6 | COOCH₂CH₃ | Cl | — | — | — | OCH₃ | N | |
| J-6 | COOCH₂CH₃ | CH₃ | — | — | — | OCH₃ | N | |
| J-6 | CH₃ | H | — | — | — | CH₃ | N | |
| J-6 | CH₃ | F | — | — | — | OCH₃ | N | |
| J-6 | CH₃ | Cl | — | — | — | CH₃ | CH | |
| J-6 | CH₃ | CH₃ | — | — | — | OCH₃ | CH | |
| J-6 | SO₂N(CH₃)₂ | H | — | — | — | OCH₃ | CH | |
| J-6 | SO₂N(CH₃)₂ | F | — | — | — | OCH₃ | CH | |
| J-6 | SO₂N(CH₃)₂ | Cl | — | — | — | CH₃ | N | |
| J-6 | SO₂N(CH₃)₂ | CH₃ | — | — | — | CH₃ | N | |
| J-6 | N(CH₃)₂ | H | — | — | — | CH₃ | CH | |
| J-6 | N(CH₃)₂ | F | — | — | — | OCH₃ | N | |
| J-6 | N(CH₃)₂ | Cl | — | — | — | CH₃ | CH | |
| J-6 | N(CH₃)₂ | CH₃ | — | — | — | OCH₃ | N | |
| J-7 | COOCH₃ | H | — | — | — | CH₃ | CH | |
| J-7 | COOCH₃ | F | — | — | — | OCH₃ | N | |
| J-7 | COOCH₃ | Cl | — | — | — | CH₃ | CH | |
| J-7 | COOCH₃ | CH₃ | — | — | — | OCH₃ | N | |
| J-7 | COOCH₂CH₃ | H | — | — | — | CH₃ | CH | |
| J-7 | COOCH₂CH₃ | F | — | — | — | CH₃ | CH | |
| J-7 | COOCH₂CH₃ | Cl | — | — | — | OCH₃ | N | |
| J-7 | COOCH₂CH₃ | CH₃ | — | — | — | OCH₃ | N | |
| J-7 | CH₃ | H | — | — | — | CH₃ | N | |
| J-7 | CH₃ | F | — | — | — | OCH₃ | N | |
| J-7 | CH₃ | Cl | — | — | — | CH₃ | CH | |
| J-7 | CH₃ | CH₃ | — | — | — | OCH₃ | CH | |
| J-7 | SO₂N(CH₃)₂ | H | — | — | — | OCH₃ | CH | |
| J-7 | SO₂N(CH₃)₂ | F | — | — | — | OCH₃ | CH | |
| J-7 | SO₂N(CH₃)₂ | Cl | — | — | — | CH₃ | N | |
| J-7 | SO₂N(CH₃)₂ | CH₃ | — | — | — | CH₃ | N | |
| J-7 | N(CH₃)₂ | H | — | — | — | CH₃ | CH | |
| J-7 | N(CH₃)₂ | F | — | — | — | OCH₃ | N | |
| J-7 | N(CH₃)₂ | Cl | — | — | — | CH₃ | CH | |
| J-7 | N(CH₃)₂ | CH₃ | — | — | — | OCH₃ | N | |
| J-8 | COOCH₃ | H | — | — | — | CH₃ | CH | |
| J-8 | COOCH₃ | F | — | — | — | CH₃ | N | |
| J-8 | COOCH₃ | Cl | — | — | — | CH₃ | CH | |
| J-8 | COOCH₃ | CH₃ | — | — | — | OCH₃ | N | |
| J-8 | COOCH₂CH₃ | H | — | — | — | CH₃ | CH | |
| J-8 | COOCH₂CH₃ | F | — | — | — | CH₃ | CH | |
| J-8 | COOCH₂CH₃ | Cl | — | — | — | OCH₃ | N | |
| J-8 | COOCH₂CH₃ | CH₃ | — | — | — | OCH₃ | N | |
| J-8 | CH₃ | H | — | — | — | CH₃ | N | |
| J-8 | CH₃ | F | — | — | — | OCH₃ | N | |
| J-8 | CH₃ | Cl | — | — | — | CH₃ | CH | |
| J-8 | CH₃ | CH₃ | — | — | — | OCH₃ | CH | |
| J-8 | SO₂N(CH₃)₂ | H | — | — | — | OCH₃ | CH | |
| J-8 | SO₂N(CH₃)₂ | F | — | — | — | OCH₃ | CH | |

TABLE X-continued

General Formula X

| J | R$_{10}$ | R$_{10}'$ | R$_{11}$ | R$_{12}$ | R$_{13}$ | R$_1$ | Z | m.p. (°C.) |
|---|---|---|---|---|---|---|---|---|
| J-8 | SO$_2$N(CH$_3$)$_2$ | Cl | — | — | — | CH$_3$ | N | |
| J-8 | SO$_2$N(CH$_3$)$_2$ | CH$_3$ | — | — | — | CH$_3$ | N | |
| J-8 | N(CH$_3$)$_2$ | H | — | — | — | CH$_3$ | CH | |
| J-8 | N(CH$_3$)$_2$ | F | — | — | — | OCH$_3$ | N | |
| J-8 | N(CH$_3$)$_2$ | Cl | — | — | — | CH$_3$ | CH | |
| J-8 | N(CH$_3$)$_2$ | CH$_3$ | — | — | — | OCH$_3$ | N | |
| J-9 | COOCH$_3$ | H | — | — | — | CH$_3$ | CH | |
| J-9 | COOCH$_3$ | F | — | — | — | OCH$_3$ | N | |
| J-9 | COOCH$_3$ | Cl | — | — | — | CH$_3$ | CH | |
| J-9 | COOCH$_3$ | CH$_3$ | — | — | — | OCH$_3$ | N | |
| J-9 | COOCH$_2$CH$_3$ | H | — | — | — | CH$_3$ | CH | |
| J-9 | COOCH$_2$CH$_3$ | F | — | — | — | CH$_3$ | CH | |
| J-9 | COOCH$_2$CH$_3$ | Cl | — | — | — | OCH$_3$ | N | |
| J-9 | COOCH$_2$CH$_3$ | CH$_3$ | — | — | — | OCH$_3$ | N | |
| J-9 | CH$_3$ | H | — | — | — | CH$_3$ | N | |
| J-9 | CH$_3$ | F | — | — | — | OCH$_3$ | N | |
| J-9 | CH$_3$ | Cl | — | — | — | CH$_3$ | CH | |
| J-9 | CH$_3$ | CH$_3$ | — | — | — | OCH$_3$ | CH | |
| J-9 | SO$_2$N(CH$_3$)$_2$ | H | — | — | — | OCH$_3$ | CH | |
| J-9 | SO$_2$N(CH$_3$)$_2$ | F | — | — | — | OCH$_3$ | CH | |
| J-9 | SO$_2$N(CH$_3$)$_2$ | Cl | — | — | — | CH$_3$ | N | |
| J-9 | SO$_2$N(CH$_3$)$_2$ | CH$_3$ | — | — | — | CH$_3$ | N | |
| J-9 | N(CH$_3$)$_2$ | H | — | — | — | CH$_3$ | CH | |
| J-9 | N(CH$_3$)$_2$ | F | — | — | — | OCH$_3$ | N | |
| J-9 | N(CH$_3$)$_2$ | Cl | — | — | — | CH$_3$ | CH | |
| J-9 | N(CH$_3$)$_2$ | CH$_3$ | — | — | — | OCH$_3$ | N | |
| J-10 | — | — | CH$_3$ | H | H | CH$_3$ | CH | |
| J-10 | — | — | CH$_3$ | H | H | CH$_3$ | N | |
| J-10 | — | — | CH$_3$ | H | H | OCH$_3$ | CH | |
| J-10 | — | — | CH$_3$ | H | H | OCH$_3$ | N | |
| J-10 | — | — | CH$_3$ | CH$_3$ | H | OCH$_3$ | CH | |
| J-10 | — | — | CH$_3$ | CH$_3$ | H | OCH$_3$ | N | |
| J-10 | — | — | CO$_2$CH$_3$ | H | H | CH$_3$ | CH | |
| J-10 | — | — | CO$_2$CH$_3$ | H | H | CH$_3$ | N | |
| J-10 | — | — | CO$_2$CH$_3$ | H | H | OCH$_3$ | CH | |
| J-10 | — | — | CO$_2$CH$_3$ | H | H | OCH$_3$ | N | |
| J-10 | — | — | SO$_2$N(CH$_3$)$_2$ | H | H | CH$_3$ | CH | |
| J-10 | — | — | SO$_2$N(CH$_3$)$_2$ | H | H | CH$_3$ | N | |
| J-10 | — | — | SO$_2$N(CH$_3$)$_2$ | H | H | OCH$_3$ | CH | |
| J-10 | — | — | SO$_2$N(CH$_3$)$_2$ | H | H | OCH$_3$ | N | |
| J-11 | — | — | CH$_3$ | H | H | CH$_3$ | CH | |
| J-11 | — | — | CH$_3$ | H | H | CH$_3$ | N | |
| J-11 | — | — | CH$_3$ | H | H | OCH$_3$ | CH | |
| J-11 | — | — | CH$_3$ | H | H | OCH$_3$ | N | |
| J-11 | — | — | CH$_3$ | CH$_3$ | H | OCH$_3$ | CH | |
| J-11 | — | — | CH$_3$ | CH$_3$ | H | OCH$_3$ | N | |
| J-11 | — | — | CO$_2$CH$_3$ | H | H | CH$_3$ | CH | |
| J-11 | — | — | CO$_2$CH$_3$ | H | H | CH$_3$ | N | |
| J-11 | — | — | CO$_2$CH$_3$ | H | H | OCH$_3$ | CH | |
| J-11 | — | — | CO$_2$CH$_3$ | H | H | OCH$_3$ | N | |
| J-11 | — | — | SO$_2$N(CH$_3$)$_2$ | H | H | CH$_3$ | CH | |
| J-11 | — | — | SO$_2$N(CH$_3$)$_2$ | H | H | CH$_3$ | N | |
| J-11 | — | — | SO$_2$N(CH$_3$)$_2$ | H | H | OCH$_3$ | CH | |
| J-11 | — | — | SO$_2$N(CH$_3$)$_2$ | H | H | OCH$_3$ | N | |
| J-11 | — | — | CH$_3$ | H | CH$_3$ | OCH$_3$ | CH | |
| J-11 | — | — | CH$_3$ | H | CH$_3$ | OCH$_3$ | N | |
| J-12 | — | — | CH$_3$ | H | H | CH$_3$ | CH | |
| J-12 | — | — | CH$_3$ | H | H | CH$_3$ | N | |
| J-12 | — | — | CH$_3$ | H | H | OCH$_3$ | CH | |
| J-12 | — | — | CH$_3$ | H | CH$_3$ | OCH$_3$ | CH | |
| J-12 | — | — | CH$_3$ | H | CH$_3$ | OCH$_3$ | N | |
| J-12 | — | — | CO$_2$CH$_3$ | H | H | CH$_3$ | CH | |
| J-12 | — | — | CO$_2$CH$_3$ | H | H | CH$_3$ | N | |
| J-12 | — | — | CO$_2$CH$_3$ | H | H | OCH$_3$ | CH | |
| J-12 | — | — | CO$_2$CH$_3$ | H | H | OCH$_3$ | N | |
| J-12 | — | — | SO$_2$N(CH$_3$)$_2$ | H | H | CH$_3$ | CH | |
| J-12 | — | — | SO$_2$N(CH$_3$)$_2$ | H | H | CH$_3$ | N | |
| J-12 | — | — | SO$_2$N(CH$_3$)$_2$ | H | H | OCH$_3$ | CH | |
| J-12 | — | — | SO$_2$N(CH$_3$)$_2$ | H | H | OCH$_3$ | N | |
| J-13 | — | — | CH$_3$ | H | H | CH$_3$ | CH | |
| J-13 | — | — | CH$_3$ | H | H | CH$_3$ | N | |
| J-13 | — | — | CH$_3$ | H | H | OCH$_3$ | CH | |
| J-13 | — | — | CH$_3$ | H | H | OCH$_3$ | N | |
| J-13 | — | — | CH$_3$ | H | CH$_3$ | OCH$_3$ | CH | |
| J-13 | — | — | CH$_3$ | H | CH$_3$ | OCH$_3$ | N | |
| J-13 | — | — | CO$_2$CH$_3$ | H | H | CH$_3$ | CH | |
| J-13 | — | — | CO$_2$CH$_3$ | H | H | CH$_3$ | N | |
| J-13 | — | — | CO$_2$CH$_3$ | H | H | OCH$_3$ | CH | |
| J-13 | — | — | CO$_2$CH$_3$ | H | H | OCH$_3$ | N | |

TABLE X-continued

| | | General Formula X | | | | | |
|---|---|---|---|---|---|---|---|
| J | $R_{10}$ | $R_{10}'$ $R_{11}$ | $R_{12}$ | $R_{13}$ | $R_1$ | Z | m.p. (°C.) |
| J-13 | — | — $SO_2N(CH_3)_2$ | H | H | $CH_3$ | CH | |
| J-13 | — | — $SO_2N(CH_3)_2$ | H | H | $CH_3$ | N | |
| J-13 | — | — $SO_2N(CH_3)_2$ | H | H | $OCH_3$ | CH | |
| J-13 | — | — $SO_2N(CH_3)_2$ | H | H | $OCH_3$ | N | |
| J-13 | — | — $SO_2N(CH_3)_2$ | $CH_3$ | H | $OCH_3$ | CH | |
| J-13 | — | — $SO_2N(CH_3)_2$ | $CH_3$ | H | $OCH_3$ | N | |

TABLE XI

| | General Formula XI | | |
|---|---|---|---|
| $R_{14}$ | $R_1$ | Z | m.p. (°C.) |
| H | $CH_3$ | CH | |
| H | $CH_3$ | N | |
| H | $OCH_3$ | CH | |
| H | $OCH_3$ | N | |
| H | $N(CH_3)_2$ | CH | |
| H | $N(CH_3)_2$ | N | |
| $CH_3$ | $CH_3$ | CH | |
| $CH_3$ | $CH_3$ | N | |
| $CH_3$ | $OCH_3$ | CH | |
| $CH_3$ | $OCH_3$ | N | |
| $CH_3$ | $N(CH_3)_2$ | CH | |
| $CH_3$ | $N(CH_3)_2$ | N | |
| $OCH_3$ | $CH_3$ | CH | |
| $OCH_3$ | $CH_3$ | N | |
| $OCH_3$ | $OCH_3$ | CH | |
| $OCH_3$ | $OCH_3$ | N | |
| $OCH_3$ | $N(CH_3)_2$ | CH | |
| $OCH_3$ | $N(CH_3)_2$ | N | |
| F | $CH_3$ | CH | |
| F | $CH_3$ | N | |
| F | $OCH_3$ | CH | |
| F | $OCH_3$ | N | |
| F | $N(CH_3)_2$ | CH | |
| F | $N(CH_3)_2$ | N | |
| Cl | $CH_3$ | CH | |
| Cl | $CH_3$ | N | |
| Cl | $OCH_3$ | CH | |
| Cl | $OCH_3$ | N | |
| Cl | $N(CH_3)_2$ | CH | |
| Cl | $N(CH_3)_2$ | N | |
| Br | $CH_3$ | CH | |
| Br | $CH_3$ | N | |
| Br | $OCH_3$ | CH | |
| Br | $OCH_3$ | N | |
| Br | $N(CH_3)_2$ | CH | |
| Br | $N(CH_3)_2$ | N | |
| $SO_2N(CH_3)_2$ | $CH_3$ | CH | |
| $SO_2N(CH_3)_2$ | CH | N | |
| $SO_2N(CH_3)_2$ | $OCH_3$ | CH | |
| $SO_2N(CH_3)_2$ | $OCH_3$ | N | |
| $SO_2N(CH_3)_2$ | $N(CH_3)_2$ | CH | |
| $SO_2N(CH_3)_2$ | $N(CH_3)_2$ | N | |
| $OSO_2CH_3$ | $CH_3$ | CH | |
| $OSO_2CH_3$ | $CH_3$ | N | |
| $OSO_2CH_3$ | $OCH_3$ | CH | |
| $OSO_2CH_3$ | $OCH_3$ | N | |
| $OSO_2CH_3$ | $N(CH_3)_2$ | CH | |
| $OSO_2CH_3$ | $N(CH_3)_2$ | N | |
| $SO_2CH_3$ | $CH_3$ | CH | |
| $SO_2CH_3$ | $CH_3$ | N | |
| $SO_2CH_3$ | $OCH_3$ | CH | |
| $SO_2CH_3$ | $OCH_3$ | N | |
| $SO_2CH_3$ | $N(CH_3)_2$ | CH | |
| $SO_2CH_3$ | $N(CH_3)_2$ | N | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE XII

| | Active Ingredient | Weight Percent* | |
|---|---|---|---|
| | | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The method of making such compositions are well known. Solutions are prepared by simply mixing the ingredients. Fine solid compositions are made by blending and, usually, griding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 3

Wettable Powder

| | |
|---|---|
| 2-[[(4-cyano-6-methylpyrimidin-2-yl)aminocarbonyl]-aminosulfonyl]benzoic acid, methyl ester | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 4

Wettable Powder

| | |
|---|---|
| 2[[(4-cyano-6-methylpyrimidin-2-yl)aminocarbonyl]-aminosulfonyl]benzoic acid, methyl ester | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 5

Granule

| | |
|---|---|
| Wettable Powder of Example 4 | 5% |
| attapulgite granules (U.S.S. 20–40 mesh; 0.84–0.42 mm) | 95% |

A slurry of wettable powder containing 25% solids is sprayed on the surface of attapulgite granules in a double-cone blender. The granules are dried and packaged.

EXAMPLE 6

Extruded Pellet

| | |
|---|---|
| 2[[(4-cyano-6-methylpyrimidin-2-yl)aminocarbonyl]-aminosulfonyl]benzoic acid, methyl ester | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 7

Oil Suspension

| | |
|---|---|
| 2[[(4-cyano-6-methylpyrimidin-2-yl)aminocarbonyl]-aminosulfonyl]benzoic acid, methyl ester | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extending with oils or emulsified in water.

EXAMPLE 8

Wettable Powder

| | |
|---|---|
| 2[[(4-cyano-6-methylpyrimidin-2-yl)aminocarbonyl]-aminosulfonyl]benzoic acid, methyl ester | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 9

Low Strength Granule

| | |
|---|---|
| 2[[(4-cyano-6-methylpyrimidin-2-yl)aminocarbonyl]-aminosulfonyl]benzoic acid, methyl ester | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 10

Aqueous Suspension

| | |
|---|---|
| 2-[[(4-cyano-6-methylpyrimidin-2-yl)aminocarbonyl]-aminosulfonyl]benzoic acid, methyl ester | 40% |

-continued

| | |
|---|---|
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 11

Solution

| | |
|---|---|
| 2-[[(4-cyano-6-methylpyrimidin-2-yl)aminocarbonyl]-aminosulfonyl]benzoic acid, methyl ester, ammonium salt | 5% |
| water | 95% |

The salt is added directly to the water with stirring to produce the solution, which may then be packaged for use.

EXAMPLE 12

Low Strength Granule

| | |
|---|---|
| 2-[[(4-cyano-6-methylpyrimidin-2-yl)aminocarbonyl]-aminosulfonyl]benzoic acid, methyl ester | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 13

Granule

| | |
|---|---|
| 2-[[(4-cyano-6-methylpyrimidin-2-yl)aminocarbonyl]-aminosulfonyl]benzoic acid, methyl ester | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 14

High Strength Concentrate

| | |
|---|---|
| 2-[[(4-cyano-6-methylpyrimidin-2-yl)aminocarbonyl]- | 99% |

-continued

| | |
|---|---|
| aminosulfonyl]benzoic acid, methyl ester | |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 15

Wettable Powder

| | |
|---|---|
| 2-[[(4-cyano-6-methylpyrimidin-2-yl)aminocarbonyl]-aminosulfonyl]benzoic acid, methyl ester | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 16

Wettable Powder

| | |
|---|---|
| 2-[[(4-cyano-6-methylpyrimidin-2-yl)aminocarbonyl]-aminosulfonyl]benzoic acid, methyl ester | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 17

Oil Suspension

| | |
|---|---|
| 2-[[(4-cyano-6-methylpyrimidin-2-yl)aminocarbonyl]-aminosulfonyl]benzoic acid, methyl ester | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 18

Dust

| | |
|---|---|
| 2-[[(4-cyano-6-methylpyrimidin-2-yl)aminocarbonyl]-aminosulfonyl]benzoic acid, methyl ester | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 19

Emulsifiable Concentrate

| | |
|---|---|
| 2-[[(4-cyano-6-methylpyrimidin-2-yl)aminocarbonyl]-aminosulfonyl]benzoic acid, methyl ester | 10% |
| chlorobenzene | 84% |
| sorbitan monostearate and polyoxyethylene condensates thereof | 6% |

The ingredients are combined and stirred to produce a solution which can be emulsified in water for application.

Utility

Test results indicate that the compounds of the present invention are active herbicides. They have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, many of the subject compounds should be useful for the selective pre- or post-emergence weed control in crops, especially wheat and rice.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.05 to 10 kg/ha, the lower rates being suggested for use on lighter soils and/or those having a low organic matter content, for selective weed control or for situations where only short-term persistence is required.

The compounds of the invention may be used in combination with any other commercial herbicide; examples of which are those of the triazine, triazole, uracil, urea, amide, diphenylether, carbamate and bipyridylium types. The compounds may also be used in combination with mefluidide.

Because the compounds of this invention have short soil residual properties, they are particularly useful to control weeds without danger of carryover injury to subsequent crops in double-cropping systems or in other situations conducive to injury of rotational crops.

The herbicidal properties of the subject compounds were discovered in a number of greenhouse tests. The test procedures and results follow.

Test A

Seeds of crabgrass (Digitaria spp.), barnyardgrass (Echinochloa crusgalli), wild oats (Avena fatua), sicklepod (Cassia obtusifolia), morninglory (Ipomoea spp.), cocklebur (Xanthium pennsylvanicum), sorghum, corn, soybean, cotton, rice, wheat and purple nutsedge (Cyperus rotundus) tubers were planted and treated preemergence with the test chemicals dissolved in a nonphytotoxic solvent. At the same time, these crop and weed species were treated with a soil/foilage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
B=burn;
D=defoliation;
E=emergence inhibition;
G=growth retardation;
H=formative effect;
U=unusual pigmentation;
X=axillary stimulation;
S=albinism; and
6Y=abscised buds or flowers.

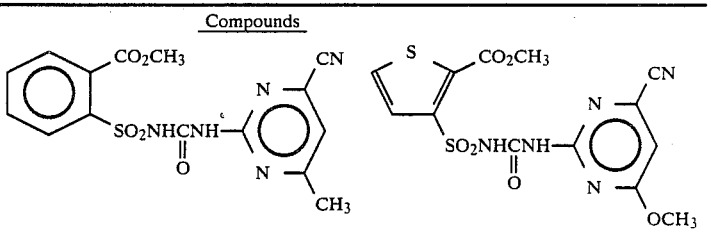

Compounds

Compound 1      Compound 2

| Rate (kg/ha) | Compound 1<br>0.05 | Compound 2<br>0.05 |
|---|---|---|
| POSTEMERGENCE | | |
| Morningglory | 2C,5G | 2C,5G |
| Cocklebur | 5C,9G | 2C |
| Velvetleaf | — | 2C,5G |
| Nutsedge | 5C,9G | 0 |
| Crabgrass | 2C,5G | 0 |
| Giant Foxtail | — | 0 |
| Barnyardgrass | 5C,9H | 3C,8H |
| Cheatgrass | — | 0 |
| Wild Oats | 3C,9G | 0 |
| Sicklepod | 3C,8H | — |
| Wheat | 2C,7G | 0 |
| Corn | 5U,9C | 0 |
| Barley | — | 0 |
| Soybean | 2C,8H | 0 |
| Rice | 3C,9G | 2G |

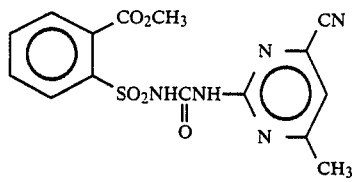

Compound 1

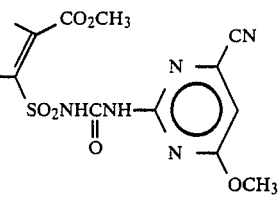

Compound 2

| Rate (kg/ha) | Compound 1 0.05 | Compound 2 0.05 |
|---|---|---|
| Sorghum | 2C,9G | 2C,9H |
| Cotton | 2G | 6G |
| Bushbean | 9C | — |
| Sugar beets | — | 3C,7G |
| PREEMERGENCE | | |
| Morningglory | 7G | 0 |
| Cocklebur | 9H | 2H |
| Velvetleaf | — | 0 |
| Nutsedge | 0 | 0 |
| Crabgrass | 0 | 0 |
| Giant Foxtail | — | 0 |
| Barnyardgrass | 6H,2C | 0 |
| Cheatgrass | — | 0 |
| Wild Oats | 2C,6G | 0 |
| Wheat | 0 | 0 |
| Corn | 2C,6G | 0 |
| Barley | — | 0 |
| Soybean | 0 | 0 |
| Rice | 2C,6G | 0 |
| Sorghum | 2C,4G | 0 |
| Sicklepod | 5G | — |
| Sugar beets | — | 2H |

What is claimed is:

1. A compound of the formula $$JSO_2NHC(W)NA \;|\; R$$

wherein
W is O or S;
R is H or $CH_3$;
A is

 A-1

$R_1$ is H, $C_1$–$C_3$ alkyl, $C_1$–$C_3$ alkoxy, $C_1$–$C_3$ haloalkoxy, $C_1$–$C_3$ haloalkyl, $C_1$–$C_3$ haloalkylthio, $C_1$–$C_3$ alkylthio, halogen, $C_2$–$C_5$ alkoxyalkyl, $C_2$–$C_5$ alkoxyalkoxy, amino, $C_1$–$C_2$ alkylamino, $N(CH_3)_2$, $C_3$ alkenyloxy, $C_3$ alkynyloxy, $C_2$–$C_3$ alkylthioalkyl, $C_2$–$C_3$ alkylsulfinylalkyl, $C_2$–$C_3$ alkylsulfonylalkyl, cyclopropyl, $C_2$–$C_3$ alkynyl,

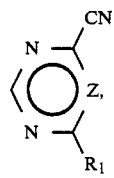

or $N(OCH_3)CH_3$;

$W_1$ and $W_2$ are independently O or S;
Z is CH;
$R_2$ is H or $CH_3$;
$R_3$ is $C_1$–$C_2$ alkyl;
$R_4$ is $C_1$–$C_2$ alkyl;
n is 2 or 3;
J is

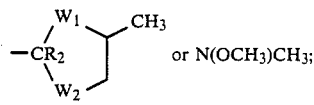

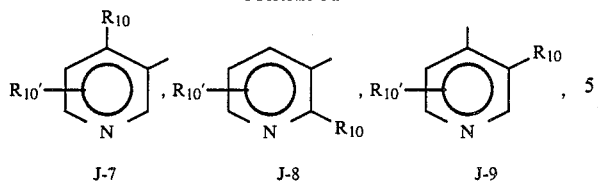

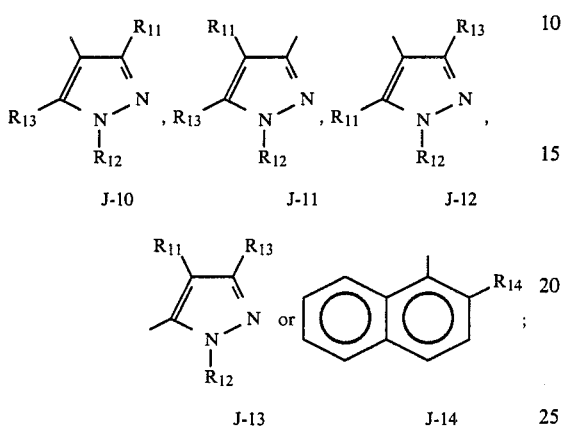

$R_5$ is F, Cl, Br, NO$_2$, C$_1$-C$_4$ alkyl, C$_2$-C$_4$ alkenyl, C$_2$-C$_4$ haloalkenyl, C$_2$-C$_4$ alkynyl, C$_1$-C$_4$ haloalkyl, C$_1$-C$_4$ alkoxy, OCH$_2$CH$_2$OCH$_3$, C$_1$-C$_4$ haloalkoxy, C$_3$-C$_4$ alkenyloxy, C$_2$-C$_4$ haloalkenyloxy, C$_3$-C$_4$ alkynyloxy, CO$_2$R$_{15}$, CONR$_{16}$R$_{17}$, SO$_2$N(OCH$_3$)CH$_3$, SO$_2$NR$_{16}$R$_{17}$, S(O)$_m$R$_{18}$, OSO$_2$R$_{19}$, C$_1$-C$_2$ alkyl substituted with C$_1$-C$_2$ alkoxy or C$_1$-C$_2$ alkylthio, CH$_2$CN, phenyl, C(O)R$_{20}$, CR$_{20}$(OR$_{21}$)$_2$,

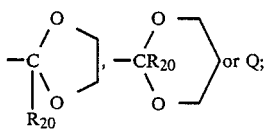

m is 0, 1 or 2;
Q is

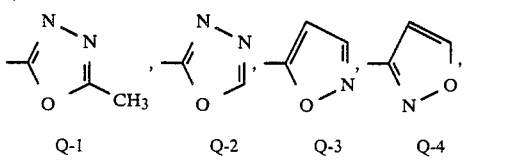

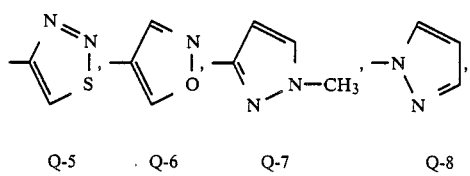

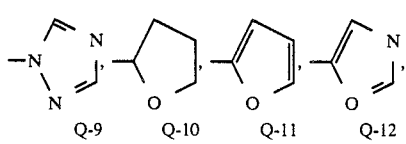

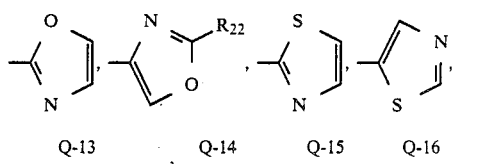

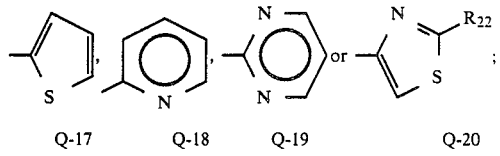

$R_6$ is H, Cl, Br, F, CN, C$_1$-C$_3$ alkyl, C$_1$-C$_3$ alkoxy, C$_1$-C$_3$ alkylthio, C$_1$-C$_3$ haloalkyl, nitro, C$_1$-C$_3$ haloalkoxy, C$_1$-C$_3$ alkylsulfinyl, C$_1$-C$_3$ alkylsulfonyl, amino, C$_1$-C$_3$ alkylamino, di(C$_1$-C$_2$)alkylamino, CH$_2$OCH$_3$ or CH$_2$SCH$_3$;

$R_7$ is Cl, NO$_2$, CO$_2$CH$_3$, CO$_2$C$_2$H$_5$, SO$_2$N(CH$_3$)$_2$, OSO$_2$CH$_3$, SO$_2$CH$_3$, SO$_2$C$_2$H$_5$, OCH$_3$ or OC$_2$H$_5$;

$R_8$ is C$_1$-C$_3$ alkyl, C$_1$-C$_2$ alkoxy, F, Cl, Br, NO$_2$, CO$_2$R$_{15}$, SO$_2$NR$_{16}$R$_{17}$, SO$_2$N(OCH$_3$)CH$_3$, C(O)NR$_{16}$R$_{17}$, S(O)$_m$R$_{18}$ or C$_2$-C$_4$ haloalkenyl;

$R_9$ is H, F, Cl or CH$_3$;

$R_{10}$ is C$_1$-C$_2$ alkyl, C$_1$-C$_2$ alkoxy, F, Cl, Br, SO$_2$NR$_{16}$R$_{17}$, SO$_2$N(OCH$_3$)CH$_3$, S(O)$_m$R$_{18}$, C(O)NR$_{16}$R$_{17}$, C$_3$-C$_4$ alkenyloxy, CH$_2$OCH$_3$, CH$_2$OC$_2$H$_5$, C$_1$-C$_2$ alkylamino, di(C$_1$-C$_2$)alkylamino or COOR$_{23}$;

$R_{10}'$ is H, F, Cl or CH$_3$;

$R_{11}$ is C$_1$-C$_3$ alkyl, F, Cl, Br, NO$_2$, CO$_2$R$_{15}$, SO$_2$NR$_{16}$R$_{17}$, SO$_2$R$_{18}$, OCF$_2$H or phenyl;

$R_{12}$ is H, C$_1$-C$_3$ alkyl, CH$_2$CH=CH$_2$ or phenyl;

$R_{13}$ is H, Cl, F, Br or C$_1$-C$_3$ alkyl;

$R_{14}$ is H, CH$_3$, OCH$_3$, F, Cl, Br, SO$_2$N(CH$_3$)$_2$, OSO$_2$CH$_3$ or S(O)$_m$CH$_3$;

$R_{15}$ is C$_1$-C$_4$ alkyl, C$_3$-C$_4$ alkenyl, C$_3$-C$_4$ alkynyl, CH$_2$CH$_2$Cl, CH$_2$CH$_2$F, CH$_2$CF$_3$, or C$_1$-C$_2$ alkyl substituted with OCH$_3$ or SCH$_3$;

$R_{16}$ is H or C$_1$-C$_3$ alkyl;

$R_{17}$ is H or C$_1$-C$_3$ alkyl;

$R_{18}$ is C$_1$-C$_3$ alkyl, CH$_2$CH=CH$_2$, CH$_2$CH≡CH or C$_1$-C$_3$ haloalkyl;

$R_{19}$ is C$_1$-C$_3$ alkyl or N(CH$_3$)$_2$;

$R_{20}$ is H, C$_1$-C$_4$ alkyl, C$_3$-C$_4$ alkenyl, C$_3$-C$_4$ alkynyl, C$_3$-C$_6$ cycloalkyl, CH$_2$CH$_2$Cl, CH$_2$CH$_2$F, CH$_2$CF$_3$ or C$_1$-C$_2$ alkyl substituted with OCH$_3$ or SCH$_3$;

$R_{21}$ is C$_1$-C$_2$ alkyl;

$R_{22}$ is H or CH$_3$; and $R_{23}$ is C$_1$-C$_3$ alkyl or allyl; and their agriculturally suitable salts; provided that (1) when W is S, then R is H, and R$_1$ is CH$_3$, OCH$_3$, OC$_2$H$_5$, CH$_2$OCH$_3$, C$_2$H$_5$, CF$_3$, SCH$_3$, OCH$_2$CH=CH$_2$, OCH$_2$C≡CH, OCH$_2$CH$_2$OCH$_3$, CH(OCH$_3$)$_2$, or

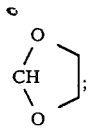

(2) when J is J-1, then R$_1$ is other than

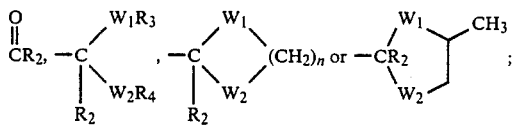

and (3) when J is J-10, then $R_{11}$ and $R_{12}$ are not both phenyl.

2. Compounds of claim 1 wherein W is O and R is H.
3. Compounds of claim 2 where $R_5$ is Cl, Br, $NO_2$, $C_1$-$C_3$ alkyl, $C_2$-$C_3$ *alkenyl*, $C_2$-$C_3$ haloalkenyl, $C_2$-$C_3$ alkynyl, $C_1$-$C_3$ haloalkyl, $C_1$-$C_3$ alkoxy, $OCH_2CH_2OCH_3$, $C_1$-$C_3$ haloalkoxy, $C_3$ alkenyloxy, $C_2$-$C_3$ haloalkenyloxy, $C_3$ alkynyloxy, $CO_2R_{15}$, $CONR_{16}R_{17}$, $SO_2N(OCH_3)CH_3$, $SO_2NR_{16}R_{17}$, $S(O)_mR_{18}$, $OSO_2R_{19}$, $C_1$-$C_2$ alkyl substituted with $C_1$-$C_2$ alkoxy or $C_1$-$C_2$ alkylthio, $CH_2CN$, phenyl, $C(O)R_{20}$, $CR_{20}(OR_{21})_2$,

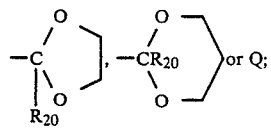

$R_6$ is H, Cl, Br, F, $CH_3$, $C_2H_5$, $OCH_3$, $OC_2H_5$, $SCH_3$, $SC_2H_5$, $C_1$-$C_2$ haloalkyl, CN, $CH_2OCH_3$ or $CH_2SCH_3$; and $R_6$ must be H when para to the sulfonylurea bridge, $SO_2NHC(W)NRA$;

Q is Q-1, Q-2, Q-5, Q-12, Q-13, Q-14, Q-15, Q-16 or Q-20;

$R_7$ is $CO_2CH_3$, $CO_2C_2H_5$, $SO_2N(CH_3)_2$, $SO_2CH_3$, $SO_2C_2H_5$;

$R_8$ is $C_1$-$C_2$ alkyl, Cl, Br, $NO_2$, $CO_2R_{15}$, $SO_2NR_{16}R_{17}$, $S(O)_mR_{18}$ or $C_2$-$C_4$ haloalkenyl;

$R_{10}$ is $C_1$-$C_2$ alkyl, $C_1$-$C_2$ alkoxy, Cl, Br, $SO_2NR_{16}R_{17}$, $S(O)_mR_{18}$, $OCH_2CH=CH_2$, $(CH_3)_2N$, $CH_3NH$ or $COOR_{23}$;

$R_{11}$ is $C_1$-$C_2$ alkyl, Cl, Br, $NO_2$, $CO_2R_{15}$, $SO_2NR_{16}R_{17}$ or $SO_2R_{18}$;

$R_{12}$ is H or $C_1$-$C_2$ alkyl;

$R_{13}$ is H, Cl, F or $CH_3$;

$R_{15}$ is $C_1$-$C_3$ alkyl, $CH_2CH=CH_2$ or $CH_2C\equiv CH$;

$R_{16}$ and $R_{17}$ are independently H, $CH_3$ or $C_2H_5$;

$R_{18}$ is $C_1$-$C_3$ alkyl or $C_1$-$C_3$ haloalkyl; and $R_{20}$ is H, $C_1$-$C_3$ alkyl, $C_3$-$C_4$ cycloalkyl, $CH_2CH=CH_2$ or $CH_2C\equiv CH$.

4. Compounds of claim 3 where $R_1$ is $C_1$-$C_2$ alkyl, $C_1$-$C_2$ alkoxy, $C_1$-$C_2$ haloalkoxy, $C_1$-$C_2$ haloalkyl, $C_1$-$C_2$ haloalkylthio, $C_1$-$C_2$ alkylthio, $C_2$-$C_3$ alkoxyalkyl, $C_2$-$C_3$ alkoxyalkoxy, $C_2$-$C_3$ alkylthioalkyl, $C_2$-$C_3$ alkylsulfinylalkyl, $C_2$-$C_3$ alkylsulfonylalkyl, cyclopropyl or $C\equiv CH$.

5. Compounds of claim 4 wherein J is J-1 and $R_6$ is in the 5-position.
6. Compounds of claim 4 wherein J is J-2.
7. Compounds of claim 4 where J is J-3 and $R_9$ is H.
8. Compounds of claim 4 where J is J-4 and $R_9$ is H.
9. Compounds of claim 4 where J is J-5 and $R_9$ is H.
10. Compounds of claim 4 where J is J-6.
11. Compounds of claim 4 where J is J-7.
12. Compounds of claim 4 where J is J-8.
13. Compounds of claim 4 where J is J-9.
14. Compounds of claim 4 where J is J-10.
15. Compounds of claim 4 where J is J-11.
16. Compounds of claim 4 where J is J-12.
17. Compounds of claim 4 where J is J-13.
18. Compounds of claim 4 wherein J is J-14.
19. The compound of claim 1 which is 2-[[(4-cyano-6-methylpyrimidin-2-yl)aminocarbonyl]aminosulfonyl]-benzoic acid, methyl ester.
20. The compound of claim 1 which is 3-[[(4-cyano-6-methoxypyrimidin-2-yl)aminocarbonyl]aminosulfonyl]2-thiophene carboxylic acid, methyl ester.
21. A composition suitable for controlling the growth of undesired vegetation which comprises an effective amount of a compound of claim 1 and at least one of the following: surfactant, solid or liquid diluent.
22. A composition suitable for controlling the growth of undesired vegetation which comprises an effective amount of a compound of claim 2 and at least one of the following: surfactant, solid or liquid diluent.
23. A composition suitable for controlling the growth of undesired vegetation which comprises an effective amount of a compound of claim 3 and at least one of the following: surfactant, solid or liquid diluent.
24. A composition suitable for controlling the growth of undesired vegetation which comprises an effective amount of a compound of claim 4 and at least one of the following: surfactant, solid or liquid diluent.
25. A method for controlling the growth of undesired vegetation which comprises applying to the locus to be protected an effective amount of a compound of claim 1.
26. A method for controlling the growth of undesired vegetation which comprises applying to the locus to be protected an effective amount of a compound of claim 2.
27. A method for controlling the growth of undesired vegetation which comprises applying to the locus to be protected an effective amount of a compound of claim 1.
28. A method for controlling the growth of undesired vegetation which comprises applying to the locus to be protected an effective amount of a compound of claim 4.

* * * * *

UNITED STATES PATENT AND TRADEMARK OFFICE
CERTIFICATE OF CORRECTION

PATENT NO. : 4,740,229
DATED : April 26, 1988
INVENTOR(S) : Thomas P. Selby

It is certified that error appears in the above-identified patent and that said Letters Patent is hereby corrected as shown below:

Column 5, line 10, Q-12 reading 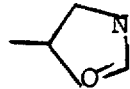 should read 

Claim 1, column 43, line 6, Q-12 reading 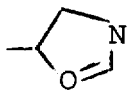 should read 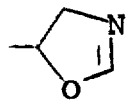

Claim 3, column 45, line 13, "$\ell$ $a\ell kenyl$, $c_2-C_3$" should read --alkenyl, $C_2-C_3$--.

Signed and Sealed this

Twenty-ninth Day of November, 1988

Attest:

DONALD J. QUIGG

Attesting Officer

Commissioner of Patents and Trademarks